US011335015B2

(12) United States Patent
Collins et al.

(10) Patent No.: US 11,335,015 B2
(45) Date of Patent: May 17, 2022

(54) SEGMENTATION OF STRUCTURES FOR STATE DETERMINATION

(71) Applicants: The Royal Institution for the Advancement of Learning/McGill University, Montreal (CA); Universitat Politècnica de València, Valencia (ES)

(72) Inventors: Donald Louis Collins, St-Lambert (CA); Pierrick Coupe, Mérignac (FR); Jose Vicente Manjon Herrera, Valencia (ES)

(*) Notice: Subject to any disclaimer, the term of this patent is extended or adjusted under 35 U.S.C. 154(b) by 144 days.

(21) Appl. No.: 16/874,370

(22) Filed: May 14, 2020

(65) Prior Publication Data
US 2020/0273186 A1 Aug. 27, 2020

Related U.S. Application Data

(63) Continuation of application No. 15/622,634, filed on Jun. 14, 2017, now abandoned, which is a (Continued)

(30) Foreign Application Priority Data

Sep. 16, 2011 (CA) .................................. CA 2752370

(51) Int. Cl.
*G06K 9/00* (2006.01)
*G06T 7/33* (2017.01)
(Continued)

(52) U.S. Cl.
CPC .............. *G06T 7/33* (2017.01); *A61B 5/0042* (2013.01); *A61B 5/055* (2013.01); *A61B 5/4088* (2013.01);
(Continued)

(58) Field of Classification Search
CPC ....................................................... G06T 7/33
See application file for complete search history.

(56) References Cited

U.S. PATENT DOCUMENTS

2004/0101181 A1 5/2004 Giger et al.
2007/0019846 A1 1/2007 Bullitt et al.
(Continued)

FOREIGN PATENT DOCUMENTS

WO  WO 2005/023086 A2  3/2005
WO  WO 2010/088763 A1  8/2010

OTHER PUBLICATIONS

Canadian Patent applicaion No. 2847600 Office Action dated Feb. 17, 2021.
(Continued)

*Primary Examiner* — Oneal R Mistry
(74) *Attorney, Agent, or Firm* — Anglehart et al.

(57) ABSTRACT

Applicants have discovered a new low-cost and accessible method and apparatus that allowing for quicker and more precise state determinations based on medical images. The method and apparatus are non-intrusive and require providing a medical image of a subject and determining a state based on a comparison to a training image set comprising two or more states. There is provided, according to the present invention, a computer-implemented method for processing medical images comprising calculating non-local means patch-based weights comparing patches surrounding pixels of interest in a test image with a number of patches of pixels surrounding a corresponding number of pixels in reference images; and calculating for the pixels of interest at least one state estimation using a given state assigned to said reference images and said weights.

4 Claims, 15 Drawing Sheets

Related U.S. Application Data continuation of application No. 15/371,781, filed on Dec. 7, 2016, now abandoned, which is a continuation of application No. 14/342,873, filed as application No. PCT/CA2012/050644 on Sep. 17, 2012, now abandoned.

(60) Provisional application No. 61/535,720, filed on Sep. 16, 2011.

(51) Int. Cl.
  *G06T 7/41* (2017.01)
  *A61B 5/055* (2006.01)
  *G06T 7/00* (2017.01)
  *A61B 5/00* (2006.01)

(52) U.S. Cl.
  CPC .............. *G06T 7/0012* (2013.01); *G06T 7/41* (2017.01); *G06T 2207/10088* (2013.01); *G06T 2207/30016* (2013.01)

(56) References Cited

U.S. PATENT DOCUMENTS

| | | | |
|---|---|---|---|
| 2008/0101665 A1* | 5/2008 | Collins | A61B 5/4088 382/128 |
| 2011/0019935 A1* | 1/2011 | Kelm | G06T 5/002 382/275 |
| 2012/0051610 A1* | 3/2012 | Avinash | G06T 11/206 382/128 |
| 2012/0053447 A1* | 3/2012 | Duchesne | A61B 5/055 600/410 |
| 2012/0070044 A1* | 3/2012 | Avinash | G06T 7/0014 382/128 |
| 2013/0131490 A1* | 5/2013 | Huston, III | G01R 33/56358 600/410 |
| 2013/0202177 A1* | 8/2013 | Bar-Aviv | G06T 11/008 382/131 |

OTHER PUBLICATIONS

Cuingnet, R., Gerardin, E., Tessieras, J., Auzias, G., Lehericy, S., Habert, M. O., Chupin, M., Benali, H., Colliot, O.: Automatic classification of patients with Alzheimer's disease from structural MRI: a comparison of ten methods using the ADNI database. Neuroimage 56, 766-781 (2011).

Buades, A., Coll, B., Morel, J. M., 2005. A non-local algorithm for image denoising. 2005 IEEE Computer Society Conference on Computer Vision and Pattern Recognition, vol. 2, Proceedings, 60-65.

Coupé, P., Yger, P., Prima, S., Hellier, P., Kervrann, C., Barillot, C., 2008. An optimized blockwise nonlocal means denoising filter for 3-D magnetic resonance images. IEEE Trans Med Imaging 27, 425-441.

Coupé, P., Manjon, J. V., Fonov, V., Pruessner, J., Robles, M., Collins, D. L., 2010. Nonlocal patch-based label fusion for hippocampus segmentation. Med Image Comput Comput Assist Intery 13, 129-136.

Sled, J. G., Zijdenbos, A. P., Evans, A. C., 1998. A nonparametric method for automatic correction of intensity nonuniformity in MRI data. IEEE Trans. Med. Imaging 17, 87-97.

Pruessner, J. C., Kohler, S., Crane, J., Pruessner, M., Lord, C., Byrne, A., Kabani, N., Collins, D. L., Evans, A. C., 2002. Volumetry of temporopolar, perirhinal, entorhinal and parahippocampal cortex from high-resolution MR images: considering the variability of the collateral sulcus. Cereb Cortex 12, 1342-1353.

Coupé, P., Fonov, V., Eskildsen, S., Manjon, J., Arnold, D., Collins, L., 2011a. Influence of the training library composition on a patch-based label fusion method: Application to hippocampus segmentation on the ADNI dataset. Alzheimer's and Dementia 7, S24-S24.

Coupé, P., Eskildsen, S. F., Manjon, J. V., Fonov, V. S., Collins, D. L.: Simultaneous segmentation and grading of anatomical structures for patient's classification: application to Alzheimer's disease. Neuroimage 59, 3736-3747 (2012).

Du, A. T., Schuff, N., Amend, D., Laakso, M. P., Hsu, Y. Y., Jagust, W. J., Yaffe, K., Kramer, J. H., Reed, B., Norman, D., Chui, H. C., Weiner, M. W., 2001. Magnetic resonance imaging of the entorhinal cortex and hippocampus in mild cognitive impairment and Alzheimer's disease. J Neurol Neurosurg Psychiatry 71, 441-447.

Zhang, D., Wang, Y., Zhou, L., Yuan, H., Shen, D., 2011. Multimodal classification of Alzheimer's disease and mild cognitive impairment. Neuroimage 55, 856-867.

Collins, D. L., Neelin, P., Peters, T. M., Evans, A. C., 1994. Automatic 3D intersubject registration of MR volumetric data in standardized Talairach space. J. Comput. Assist. Tomogr. 18, Abstract.

Nyul, L. G., Udupa, J. K., 2000. Standardizing the MR image intensity scales: making MR intensities have tissue specific meaning. Medical Imaging 2000: Image Display and Visualization 1, Abstract.

Nyul, L. G., Udupa, J. K., On standardizing the MR image intensity scale, Magnetic Resonance in Medicine 42:1072-1081, First published: Nov. 23, 1999.

Canadian Patent applicaion No. 2752370 Office Action dated Jul. 17, 2017.

Canadian Patent applicaion No. 2752370 Office Action dated Jun. 19, 2018.

Canadian Patent applicaion No. 2752370 Office Action dated Mar. 1, 2019.

Canadian Patent applicaion No. 2752370 Office Action dated Mar. 10, 2020.

Canadian Patent applicaion No. 2847600 Office Action dated Feb. 22, 2016.

Colliot et al., Discrimination between Alzheimer disease, mild cognitive impairment, and normal aging by using automated segmentation of the hippocampus. Radiology 248, 194-201.

Coupe et al., Patch-based segmentation using expert priors: Application to hippocampus and ventricle segmentation, NeuroImage vol. 54 Issue 2, Jan. 15, 2011, pp. 940-954.

Cuingnet et al.: Automatic classification of patients with Alzheimer's disease from structural MRI: a comparison of ten methods using the ADNI database. Neuroimage 56, 766-781 (2011).

Frisoni, G.B., Fox, N.C., Jack, C.R., Scheltens, P., Thompson, P.M., 2010. The clinical use of structural MRI in Alzheimer disease. Nature Reviews Neurology 6, 67-77.

Gerardin, et al., Multidimensional classification of hippocampal shape features discriminates Alzheimer's disease and mild cognitive impairment from normal aging. Neuroimage 47, 1476-1486.

International application No. PCT/CA2012/050644 International Preliminary Report on Patentability Chapter I dated Mar. 18, 2014.

International application No. PCT/CA2012/050644 International Search Report dated Jan. 17, 2013.

Simon Eskildsen et al., BEaST: Brain extraction using multiresolution nonlocal segmentation, HAL Id: hal-00614307 https://hal.archives-ouvertes.fr/hal-00614307, Submitted on Aug. 11, 2011.

Wolz et al., Measurement of hippocampal atrophy using 4D graph-cut segmentation: application to ADNI. Neuroimage 52, 109-1 18.

Wolz et al., Multi-method analysis of MRI images in early diagnostics of Alzheimer's disease. PLoS One 6, e25446 (2011).

Yushkevich et al., Nearly automatic segmentation of hippocampal subfields in in vivo focal T2-weighted MRI. Neuroimage 53, 1208-1224.

International application No. PCT/CA2012/050644 Written Opinion of the International Searching Authority dated Jan. 17, 2013.

Collins, D. L., Neelin, P., Peters, T. M., Evans, A. C., 1994. Automatic 3D intersubject registration of MR volumetric data in standardized Talairach space. J. Comput. Assist. Tomogr. 18 (Abstract has been submitted on Mar. 8, 2021, and the full text is attached herewith.).

\* cited by examiner

Rendered 3D frontal view of segmented HC + EC from CN subject

CN subject (ID 34)

|  | Grade | volume |
|---|---|---|
| Left HC | 0.65 | 3.73 cc$^3$ |
| Right HC | 0.51 | 3.87 cc$^3$ |
| Left EC | 0.74 | 0.36 cc$^3$ |
| Right EC | 0.58 | 0.26 cc$^3$ |

Rendered 3D frontal view of segmented HC + EC from AD subject

| AD subject (ID 73) | Grade | volume |
|---|---|---|
| Left HC | -0.72 | 2.89 cc$^3$ |
| Right HC | -0.63 | 2.73 cc$^3$ |
| Left EC | -0.62 | 0.29 cc$^3$ |
| Right EC | -0.26 | 0.32 cc$^3$ |

SEGMENTATION OF STRUCTURES FOR STATE DETERMINATION

TECHNICAL FIELD

The present invention relates generally to medical image processing. More specifically, the invention relates to methods and apparatuses for determining a state of health or disease using patch-based segmentation and grading of image structures.

BACKGROUND

The atrophy of medial temporal lobe structures, such as the hippocampus (HC) and entorhinal cortex (EC), is disease specific and serves as an early biomarker of Alzheimer's disease (AD). In particular, atrophy of the HC and the EC can be used as a marker of AD progression since changes in these structures are closely related to changes in cognitive performance of the subject. The evaluation of structure atrophy is usually estimated by volumetric studies on anatomical MRI, requiring a segmentation step that can be very time consuming when done manually.

In recent years, numerous methods have been proposed to automatically segment the hippocampus. Among these methods, several have been used to classify AD patients using HC volume, such as Colliot et al. [Colliot, O., Chetelat, G., Chupin, M., Desgranges, B., Magnin, B., Benali, H., Dubois, B., Garnero, L., Eustache, F., Lehericy, S., 2008. Discrimination between Alzheimer disease, mild cognitive impairment, and normal aging by using automated segmentation of the hippocampus. Radiology 248, 194-201]. Despite the high segmentation accuracy of the new HC segmentation approaches, using the HC volume enables a separation between AD and cognitively normal (CN) subjects with a success rate of only around 72-74% over the entire Alzheimer's Disease Neuroimaging Initiative (ADNI) database. This limited capability to classify AD patients using the HC volume only, may be due to a simplification of the complex atrophy patterns to a volume—a simple scalar. Recently, several shape analysis methods have been proposed to capture detailed HC structural modifications in order to obtain a more accurate classification. At 77%, the approach proposed in Gerardin et al. [Gerardin, E., Chetelat, G., Chupin, M., Cuingnet, R., Desgranges, B., Kim, H. S., Niethammer, M., Dubois, B., Lehericy, S., Garnero, L., Eustache, F., Colliot, O., 2009. Multidimensional classification of hippocampal shape features discriminates Alzheimer's disease and mild cognitive impairment from normal aging. Neuroimage 47, 1476-1486] yields a slightly better classification than a volumetric approach. Therefore, development of new methods capable of estimating subtle anatomical modifications of HC appear to be a critical point to obtain better classification rates. Longitudinal approaches to the AD classification problem have also been investigated by estimating the HC atrophy rate over time. In Wolz et al. (2010) [Wolz, R., Heckemann, R. A., Aljabar, P., Hajnal, J. V., Hammers, A., Lotjonen, J., Rueckert, D., 2010. Measurement of hippocampal atrophy using 4D graph-cut segmentation: application to ADNI. Neuroimage 52, 109-118], the authors reported a correct classification rate of 82% on 568 images of the ADNI dataset. However, this type of approach requires several time-points for a given patient. Finally, an emerging method is to segment subfields of the hippocampus, as taught in Yushkevich et al. [Yushkevich, P. A., Wang, H., Pluta, J., Das, S. R., Craige, C., Avants, B. B., Weiner, M. W., Mueller, S., 2010. Nearly automatic segmentation of hippocampal subfields in in vivo focal T2-weighted MRI. Neuroimage 53, 1208-1224]. This approach is potentially able to detect more detailed atrophic patterns. However, ultra-high resolution MRI is required, what is not yet the standard in clinical practice and thus limits the practical applicability of this approach for the moment. The EC volume has also been investigated as a possible biomarker to detect AD. EC atrophy seems to appear slightly earlier in AD progression than HC atrophy, and thus could be used as a more specific biomarker in the initial stages of the disease, as reviewed in Frisoni et al. [Frisoni, G. B., Fox, N.C., Jack, C. R., Scheltens, P., Thompson, P. M., 2010. The clinical use of structural MRI in Alzheimer disease. Nature Reviews Neurology 6, 67-77]. However, the high inter-subject variability of the EC and the difficulty to define the EC boundary in anatomical MRI make volumetric studies on EC very challenging. Therefore, studies based on EC volume have been limited to comparison of manual segmentations. Patient classification accuracy using EC volume varies greatly according to the dataset, from 67% up to 87% reported in the literature. It seems that the theoretical advantage of EC measurements over HC measurements is badly impacted by the difficulty to segment EC due to the ambiguity in defining its boundary in MRI. The development of automatic methods to segment EC is challenging. However, an accurate and consistent EC segmentation method could have an important impact on the use of this structure on large datasets and in a more systematic manner within the study of AD.

From a clinical point a view, AD prediction (i.e., the differentiation of progressive mild cognitive impairment (MCIp) vs. stable MCIs) can be a more crucial question than diagnosis, but this question is clearly more clinically challenging since the anatomical changes that need to be detected are more subtle. Recently, this problem has been studied using image analysis such as HC volume, Cortical Thickness measurement (CTH), Voxel Based Morphometry (VBM) and Tensor Based Morphometry (TBM). Comparison of these imaging biomarkers can be found in the publications of Wolz et al. (2011) [(Wolz, R., Julkunen, V., Koikkalainen, J., Niskanen, E., Zhang, D. P., Rueckert, D., Soininen, H., Lotjonen, J.: Multi-method analysis of MRI images in early diagnostics of Alzheimer's disease. PLoS One 6, e25446 (2011)] and Cuingnet et al. [Cuingnet, R., Gerardin, E., Tessieras, J., Auzias, G., Lehericy, S., Habert, M. O., Chupin, M., Benali, H., Colliot, O.: Automatic classification of patients with Alzheimer's disease from structural MRI: a comparison of ten methods using the ADNI database. Neuroimage 56, 766-781 (2011)]. According to these comparisons, the accuracy of AD prediction of the compared methods (e.g., HC volume, CTH, VBM or TBM) is inferior to 66% (Wolz et al 2011). To the best of our knowledge, the highest accuracy obtained on the entire ADNI database has been obtained by combining four methods resulting in 68% of accuracy for progressive forms of mild cognitive impairment (MCIp) vs. stable forms of mild cognitive impairment (MCIs) (Wolz et al. 2010).

It is therefore highly desirable to provide new methods and apparatuses that allow simultaneous patch-based segmentation and grading of images for determining a state of health or disease of a patient. It is also highly desirable to provide more efficient determination of progressive versus stable mild cognitive impairment (MCI) than what is currently available.

SUMMARY

Applicants have discovered an innovative approach to robustly and accurately detect Alzheimer's disease (AD) and prodromal forms of AD based on the distinction of specific atrophic patterns of anatomical structures such as hippocampus (HC) and entorhinal cortex (EC) in regions of interest of an image. The discovery allows to efficiently determine a pathological state of a test image using the grading of pixels of interest when compared (weighted) to images from a reference library having pre-defined states. The discovery simultaneously performs segmentation and grading of structures to efficiently capture the anatomical alterations caused by AD and other neurodegenerative diseases. Based on a nonlocal patch-based framework, the grading measure estimates the similarity of the patch surrounding the voxel under study with all the patches present in different training populations. One advantage of the present invention is that the computing-intensive calculations used for weighing the pixels of interest are done only once and used both for the segmentation of a structure of interest as well as for the grading of that structure.

The training library in some of the examples below was composed of two populations: 50 cognitively normal subjects (CN) and 50 patients with AD, randomly selected from the Alzheimer's Disease Neuroimaging Initiative (ADNI) database (www.loni.ucla.edu/ADNI). During applicants' experiments, the classification accuracy of patients (CN versus AD) using several biomarkers was compared: HC and EC volumes, the grade (defined below) of these structures and finally the combination of their volume and their grade. Tests were completed in a leave-one-out framework using discriminant analysis. First, applicants showed that biomarkers based on HC provide better classification accuracy than biomarkers based on EC. Second, applicants demonstrated that structure grading is a more powerful measure than structure volume to distinguish both populations with a classification accuracy of 90%. Finally, by adding the ages of subjects in order to better separate age-related structural changes from disease-related anatomical alterations, applicants obtained a classification accuracy of 93%.

In addition, the applicants completed tests on magnetic resonance imaging data of subjects with mild cognitive impairment to determine which subjects would remain stable (MCIs n=75) and which subjects would progress to AD (MCIp n=75) within a fixed period of time (12 months). Two training libraries were evaluated. The first contained 50 cognitively normal subjects (CN) and 50 patients with AD, randomly selected from the ADNI database. The second contained 75 MCIp and 75 MCIs, randomly selected from the ADNI database. Classification accuracy (MCIp versus MCIs) using several biomarkers was compared using both databases: HC and EC volumes, the grade of these structures, subject age and finally the combination of their volume and their grade and age. Tests were completed in a leave-one-out framework using linear discriminant analysis.

It is therefore an object of the present invention to provide a computer-implemented method for processing medical images, the method comprising calculating non-local means patch-based weights comparing patches surrounding pixels of interest in a test image with a number of patches of pixels surrounding a corresponding number of pixels in reference images and calculating for the pixels of interest at least one state estimation using given states assigned to reference images and using the weights.

In some embodiments of the present invention, pixels of interest define a region of interest (ROI) of the test image and the region of interest comprises a structure that changes with the state, such as certain parts of the hippocampus which atrophy with Alzheimer's disease. In some embodiments, the state can be the state of being, or not, a pixel that is part of a structure of interest (segmentation), or the state can be a pathological state of a pixel that shows a greater resemblance to one of the two states such as cognitively impaired and cognitively normal (grading). A state according to the present invention can also be prognostic, such as a likelihood of progressing from mild cognitive impairment to Alzheimer's disease. The ROI can be automatically determined using methods known in the art and such as averaging several structures from a template library and then further increasing a size of the ROI to ensure capturing even an above average sized structure in a test image.

In other embodiments of the present invention, pre-processing is performed prior to calculating said segmentation and/or said grading and can comprise at least one of image format conversion, denoising, regridding, correcting intensity inhomogeneity, registration to a library image, isotropic resampling, intensity clamping, intensity standardization and non-linear alignment.

In yet other embodiments of the present invention, a patch from a reference image used in the calculations is selected according to its relatedness to a test patch surrounding the pixel of interest and the relatedness can be determined by a mean and a standard deviation of intensity values of the test patch pixels and the reference patch pixels. Such embodiments allow for the segmentation of a structure from an image or from a region of interest.

In other embodiments of the present invention, the state determination comprises a structure label for each pixel of the reference images, and the value provides segmentation of the test image and a determination of the volume of the segmented structure. In other embodiments of the present invention, grading of the pixels of interest in the test image, where the pixels of interest define a segmented structure, allow for a state determination which comprises a pathological state (such as Alzheimer's disease).

In other embodiments of the present invention, state estimation comprises a pathological state of patients related to the reference images, and the method provides segmentation and pathological state grading of the pixels of interest in the test image. In other embodiments, a pathological state score is calculated from the grading of the pixels of interest, or from the grading of the pixels of interest having a predetermined segmentation.

It is another object of the present invention to provide an apparatus for processing medical images comprising a nonlocal means patch-based weight calculator for calculating a weight of a pixel of interest in a test image with a number of patches of pixels surrounding a corresponding number of pixels in a reference image; and a state calculator for calculating a state of the pixel of interest based on a given state assigned to the reference image.

In some embodiments of the present invention, the state comprises a structure label for each pixel of the reference images, and the apparatus provides segmentation of the test image.

In other embodiments of the present invention, the state comprises a pathological state of patients related to the reference images, and the apparatus provides pathological state grading of the pixels of interest in the test image.

In yet other embodiments of the present invention, an image pre-processor pre-processes the images prior to the calculating, and in still other embodiments, a test image state/label calculator calculates a state/label of the pixel of interest using the weight, and in still other embodiments, a test image state/grade calculator calculates a state/grade of the pixel of interest using the pathological state and the weight of the reference images and can generate a pathological state score based on the labels and the grades.

In yet other embodiments of the present invention, there is provided a system for processing medical images comprising a medical imager for generating a test image, an apparatus for segmenting and grading medical images and determining a pathological state determination of said test image according to the present invention and a client application for receiving and presenting data provided by said apparatus, wherein said imager, apparatus and client application communicate data over a network and return to said client application a pathological state determination.

In some aspects of the present invention, there is provided a method of selecting patients for a clinical trial based on a "state/grade" obtained in the simultaneous segmentation and grading estimation according to the present invention.

In other aspects of the present invention, there is provided a method of selecting a subject that is more likely to respond to a particular drug comprising the steps of processing the subject's image according to the present invention, where a first state (such as responders) is given to the images of patients that are known to have responded to the drug and a second state (such as non-responders) is given to patients that are known not to have responded to a particular drug.

BRIEF DESCRIPTION OF THE DRAWINGS

The invention will be better understood by way of the following detailed description of embodiments of the invention with reference to the appended drawings, in which.

DETAILED DESCRIPTION

Figure 1:
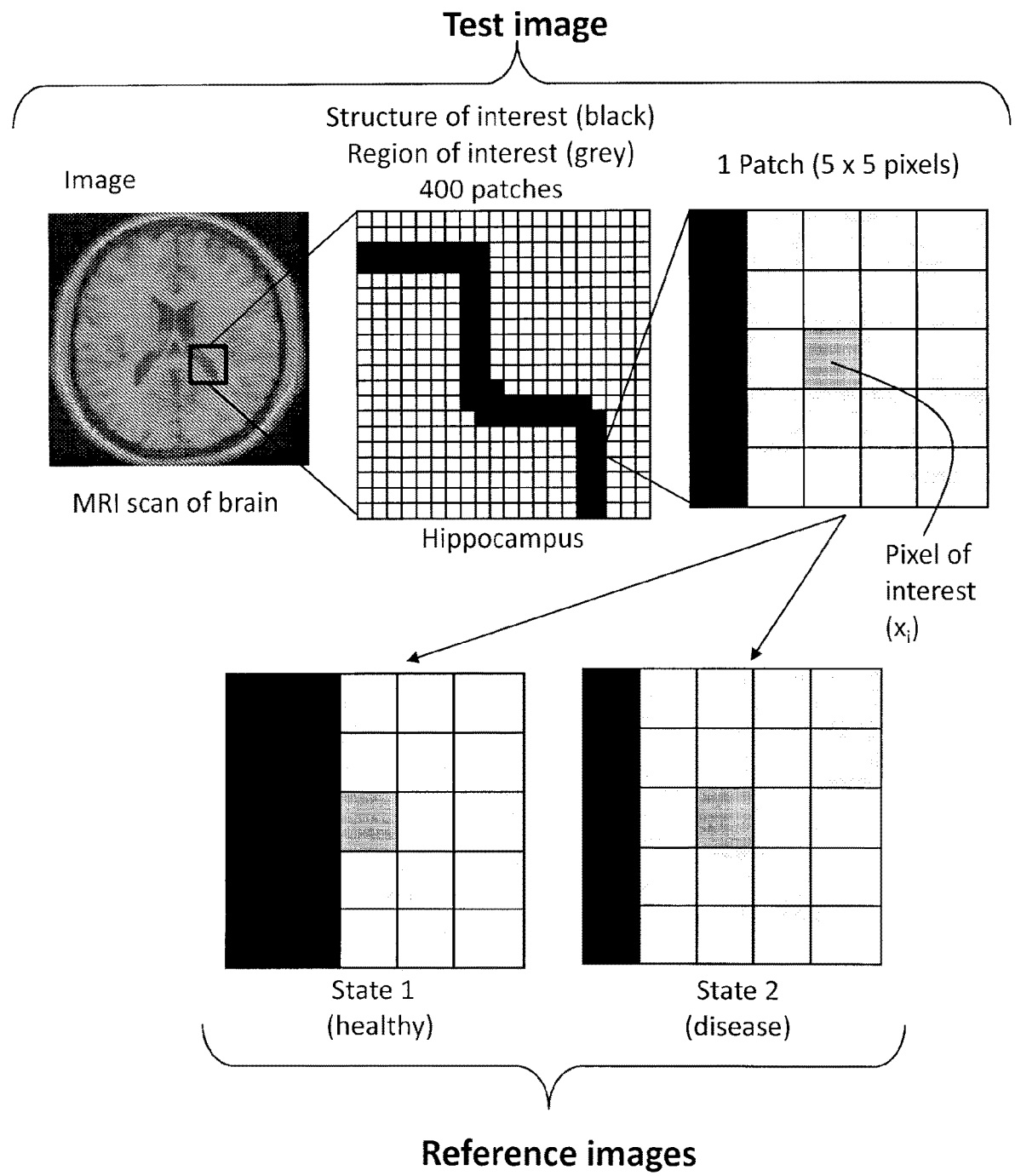
FIG. 1 is a highly schematic drawing of methods according to the present invention.

Applicants discovered a new approach designed to: i) obtain a more detailed detection of structural changes caused by the disease and ii) to perform the automatic segmentation of complex structures such as the entorhinal cortex (EC). Buades et al, [Buades, A., Coll, B., Morel, J. M., 2005. A non-local algorithm for image denoising. 2005 IEEE Computer Society Conference on Computer Vision and Pattern Recognition, Vol 2, Proceedings, 60-65] showed nonlocal means estimators for image denoising purposes. Applicants propose a new nonlocal patch-based label fusion method to segment anatomical structures as shown in Coupé et al. [Coupé, P., Manjon, J. V., Fonov, V., Pruessner, J., Robles, M., Collins, D. L., 2011b. Patch-based segmentation using expert priors: application to hippocampus and ventricle segmentation. Neuroimage 54, 940-954]. By taking advantage of pattern redundancy present within the subject's image, as well as the redundancy across training subjects, the nonlocal means scheme enables robust use of a large number of samples during estimation. In Coupé et al. (2011b), applicants applied this approach to patch-based label fusion for the segmentation of anatomical structures such as the hippocampus (HC) of healthy subjects and lateral ventricles of patients with Alzheimer's disease (AD). Applicants propose an extension of this patch-based segmentation method in order to evaluate the similarity (in the nonlocal means sense) of the intensity content of one test magnetic resonance image (MRI) compared to several training populations. By using training populations with different clinical/pathological states (e.g., healthy cognitively normal (CN) subjects and subjects/patients with Alzheimer's disease (AD)), a nonlocal means estimator is used to evaluate the proximity (i.e., the grade of the disease or the degree of anatomical change consistent with disease in the case of AD) of each voxel of the MRI under study compared to the training populations (see FIG. 2). Since the grade estimation and the label fusion steps require the same patch comparison step, simultaneous segmentation and grading of the studied structure can be achieved in one pass without extra computation. In the proposed approach, the nonlocal patch-based comparison is used to i) efficiently fuse the labels of MRI in a training database in order to segment EC and HC (or other anatomical structures), and simultaneously aggregate the clinical state of the populations constituting the training database (reference images) in order to detect the presence (or not) of the disease. Finally, the average grading value obtained over the segmented structures is proposed as a new biomarker to estimate the clinical state of the subject under study as a computerized aid to diagnosis. This invention: i) introduces an innovative approach to better characterize the patterns of structural modification caused by the disease (e.g., anatomical changes such as atrophy in case of AD) through the new concept of grading, presents a method to automatically and simultaneously perform the segmentation and the grading of EC and HC, and iii) demonstrates that the proposed approach can be used as a novel biomarker to efficiently achieve patient classification in the context of AD.

To facilitate comparison with previous work, the 1.5T baseline scans used here are the same as those used in Wolz et al. (2011), where the 834 available baseline ADNI scans were divided into 4 populations for CN, progressive MCI (MCIp), stable MCI (MCIs) and AD. An MCI subject is considered as progressive if he or she converted to AD at the date of July 2011. The four groups contained 231 CN, 238 MCIs, 167 MCIp and 198 AD. Demographic details of the used dataset can be found in Table 1.

TABLE 1

Demographic details of the four groups analyzed: patients with AD (AD), cognitively normal subjects (CN), patients with progressive mild cognitive impairment (MCIp) and patients with stable mild cognitive impairment.

|      | Population size | % males | Age ± std  | MMSE ± std |
|------|-----------------|---------|------------|------------|
| CN   | 231             | 52%     | 76.0 ± 5.0 | 29.1 ± 0.9 |
| MCIs | 238             | 67%     | 74.9 ± 7.7 | 27.2 ± 2.5 |
| MCIp | 167             | 60%     | 74.5 ± 7.2 | 26.4 ± 2.0 |
| AD   | 198             | 50%     | 75.6 ± 7.7 | 22.8 ± 2.9 |

Scoring of structures considered for analysis is achieved by estimating the nonlocal similarity of the subject structures under study with different training populations. Thanks to the nonlocal framework, the Scoring by Nonlocal Image Patch Estimator (SNIPE) handles the inter-subject variability by enabling a one-to-many mapping between the subject's anatomy and the anatomies of many training templates. Moreover, enabled by the patch-based comparison principle, SNIPE detects subtle changes caused by the disease. Applicants show the high success rate accuracy of SNIPE for AD detection (i.e., AD patients vs. cognitively normal (CN) subjects) on a subset of the ADNI database (i.e., 100 subjects).

FIG. 1 shows a highly schematic drawing of methods according to the present invention. An image acquisition system acquires a test image (FIG. 1—top left), in this case, an MRI scan of a subject's brain. Information obtained from scan data relating to specific brain structures such as the hippocampus (FIG. 1—top middle) are indicative (i.e can serve as biomarkers) for mild cognitive impairment (MCI) and Alzheimer's disease (AD). The area shown on the scan is for illustrative purposes and is not actually the hippocampus. The area blown up is shown as a 20×20 square (of 400 patches) where the hippocampus is shown in black and two square regions of interest (ROI) are highlighted in grey. One patch (FIG. 1—top middle) is further blown up to the pixel level as a 5×5 square (it should actually be understood as being a volume of 5×5×5 voxels). The computer implemented method according to the present invention identifies patches within the region of interest in order to compare the patches with many (or in some case only with the most related) patches from a healthy subject (state 1) and a diseased subject (state 2). A modification of the Buades nonlocal means estimator allows to determine if the portion of the hippocampus identified in the region of interest resembles more that of a healthy or a diseased reference image taken from a reference image library that contains examples of both states. In the schematic example shown, (FIG. 1 bottom images), it is clear that the test subject patch shows a greater resemblance to state 2, suggesting that the test image hippocampus has atrophied as a consequence of MCI or Alzheimer's disease. It will be understood that FIG. 1 is highly simplified. For example, it should be understood that all pixels of an area of interest can be segmented and/or graded and not just the central pixel of a patch. In other words, each patch is centered on a pixel but the patches for successive pixels overlap with each other. It will also be appreciated that the 2 states (healthy and diseased) are not represented by only 2 patches, but that each state is represented by an ensemble of patches where weightings/states determine the result.

The nonlocal means estimator: The nonlocal means filter was first introduced by Buades for the purpose of image denoising. In nonlocal means-based approaches as taught in Buades et al. (2005) and Coupé et al. [Coupé, P., Yger, P., Prima, S., Hellier, P., Kervrann, C., Barillot, C., 2008. An optimized blockwise nonlocal means denoising filter for 3-D magnetic resonance images. IEEE Trans Med Imaging 27, 425-441], the patch $P(x_i)$ surrounding the voxel $x_i$ under study is compared with all the patches $P(x_j)$ of the image $\Omega$ (or a subpart of the image) whatever their spatial distance to $P(x_i)$ (i.e., this is the meaning of the term "nonlocal"). According to the patch similarity between $P(x_i)$ and $P(x_j)$, estimated by the sum of squared differences (SSD) measure, each patch receives a weight $w(x_i, x_j)$:

$$w(x_i, x_j) = e^{\frac{-\|P(x_i)-P(x_j)\|_2^2}{h^2}} \quad (1)$$

where $\|\cdot\|_2$ is the L2-norm computed between each intensity of the elements of the patches $P(x_i)$ and $P(x_{s,j})$, and $h^2$ is the smoothing parameter of the weighting function. This weighting function is designed to give a weight close to 1 when the SSD is close to zero and a weight close to zero with the SSD is high. Many other functions can be used like mutual information, cross correlation, normalized cross correlation and SSD is used in this example because it is computationally light.

Finally, all the intensities $u(x_j)$ of the central voxels of the patches $P(x_j)$ are aggregated through a weighted average using the weights $w(x_i, x_j)$. In this way, the denoised intensity $\hat{u}(x_i)$ of the voxel $x_i$ can be efficiently estimated:

$$\hat{u}(x_i) = \frac{\sum_{j \in \Omega} w(x_i, x_j) u(x_j)}{\sum_{j \in \Omega} w(x_i, x_j)} \quad (2)$$

Despite its simplicity, the nonlocal means filter has been demonstrated to have excellent denoising performance. This filter is currently one of the most studied denoising filters. The efficiency of the nonlocal means filter relies on two aspects: the pattern redundancy present in an image (i.e., its self-similarity) and the robust detection of samples derived from the same population by using local context (i.e., patch-based comparison):

First, to improve the accuracy of an estimator, it is possible to reduce the committed error by increasing the number of involved samples. By using an infinite number of samples derived from the same population, the error theoretically converges to zero. To drastically increase the number of samples used, the nonlocal means filter can take advantage of the redundancy of information by using all the similar voxels present over the entire image.

Second, to ensure that the used samples are derived from the same population, the surrounding neighbour of a voxel can be used to robustly detect similar realizations of the same process. In the nonlocal means approach, this task is achieved by patch-based comparison using SSD. Two voxels with similar surrounding patches are considered as similar and to belong to the same population. More precisely, the nonlocal means filter performs patch comparison to estimate the degree of the similarity between two voxels. This way, each involved sample has a weight (see Eq. 1) reflecting its relevance.

Finally, a simple weighted average (see Eq. 2) is used to aggregate the samples according to their relevance. This way, the resulting estimator embodies the two interesting qualities described above: to build on a large number of samples and to ensure that the involved samples are derived from the same population.

From denoising to segmentation. In Coupé et al. [Coupé, P., Manjon, J. V., Fonov, V., Pruessner, J., Robles, M., Collins, D. L., 2010. Nonlocal patch-based label fusion for hippocampus segmentation. Med Image Comput Comput Assist Interv 13, 129-136.], applicants were the first to introduce the nonlocal means estimator in the context of segmentation by averaging labels instead of intensities. By using a training library of N subjects, whose segmentations of structures are known, the weighted label fusion is estimated as follows:

$$v(x_i) = \frac{\sum_{s=1}^{N} \sum_{j \in \Omega} w(x_i, x_{s,j}) \cdot l(x_{s,j})}{\sum_{s=1}^{N} \sum_{j \in \Omega} w(x_i, x_{s,j})} \quad (3)$$

where $l(x_{s,j})$ is the label (i.e., 0 for background and 1 for structure) given by the expert to the voxel $x_{s,j}$ at location j in training subject s. It has been shown that the nonlocal means estimator $v(x_i)$ provides a robust estimation of the expected label at $x_i$. With a label set of $\{0,1\}$ voxels with value $v(x_i) \geq 0.5$ are considered as belonging to the considered structure and the remaining voxels as background.

In Coupé et al. (2010, 2011b), applicants showed that accurate segmentations of anatomical structures can be obtained using this simple patch-based label fusion framework. In addition, to take advantage of the self-similarity of the image as done for denoising, the nonlocal label fusion also relies on inter-subject anatomical consistency. Therefore, many similar patches (self-similarity) can be found in every training subject (inter-subject consistency), thus improving the final estimation. Finally, compared to atlas-based methods using nonlinear registration, the nonlocal patch-based approach has the advantage of better handling the inter-subject variability problem. Contrary to the one-to-one correspondence assumed by nonlinear warping methods, the nonlocal means estimator makes it possible to deal with one-to-many mappings, which better captures the link between subjects' anatomies. This interesting aspect of the nonlocal means estimator has been used to improve video super-resolution without explicit estimation of inter-frame motion.

From Segmentation to Grading.

Figure 2:
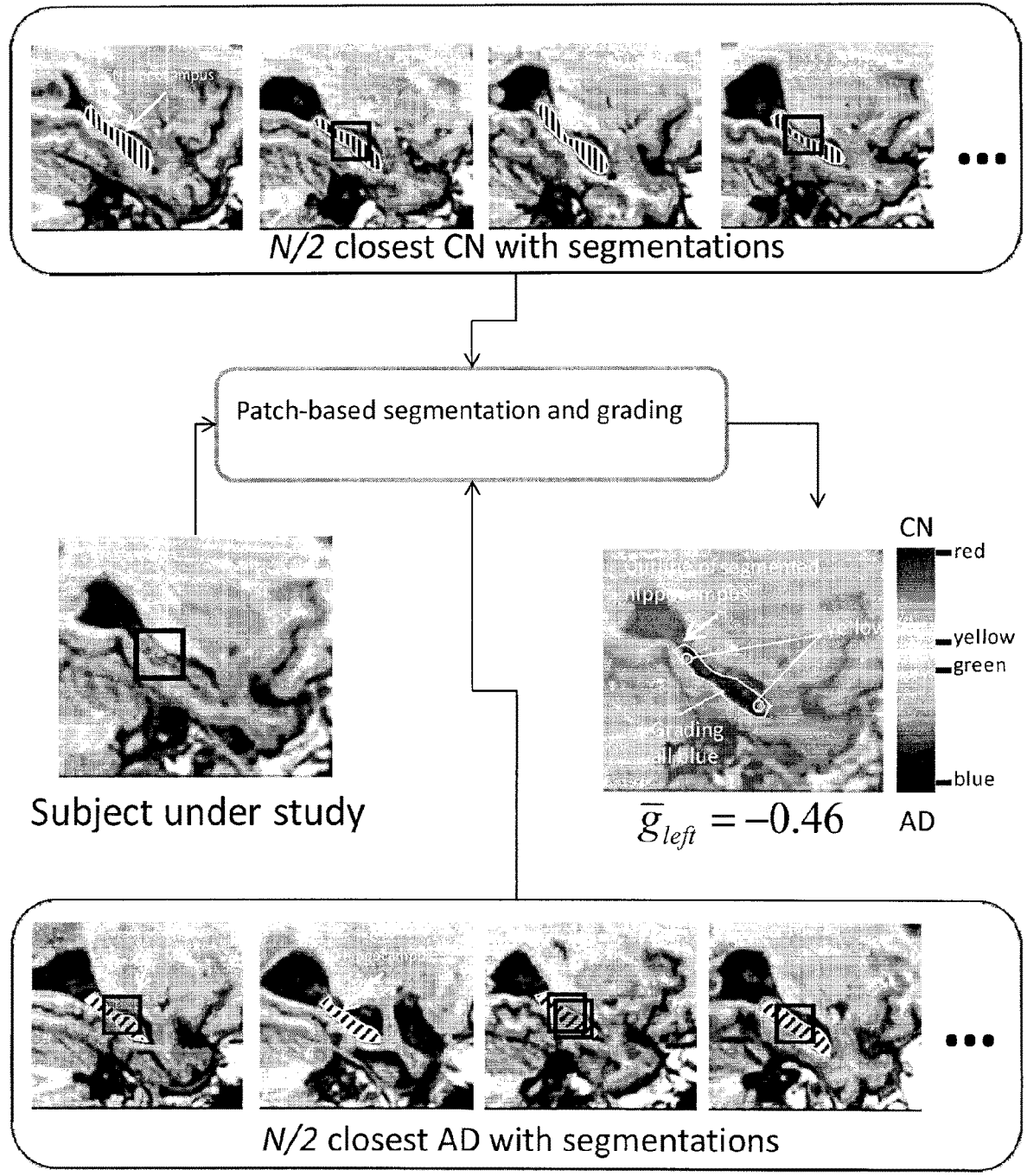
FIG. 2 shows a general summarized overview of the segmentation and grading method.
Figure 3A:
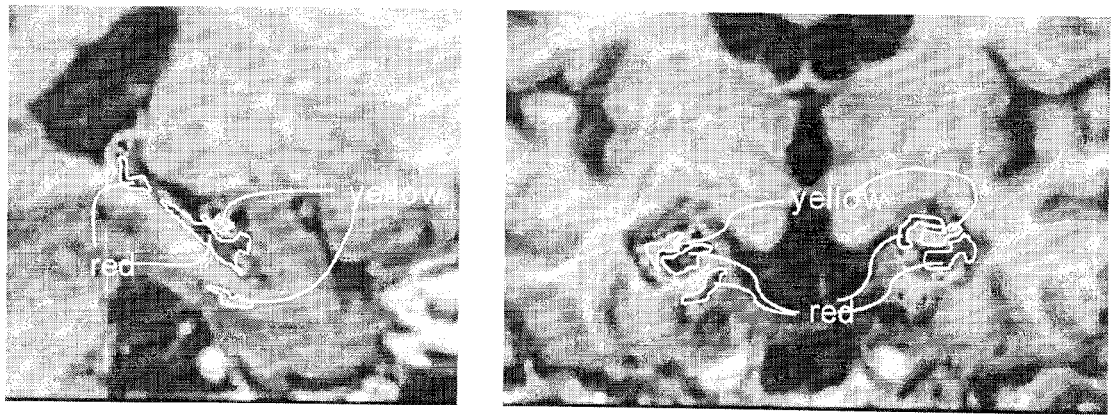
FIG. 3 shows sample segmentations and gradings of a control patient (3a) and an Alzheimer's disease patient (3b).
Figure 3A:
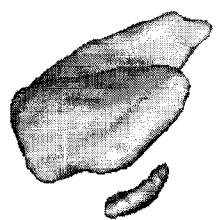
Figure 3A:
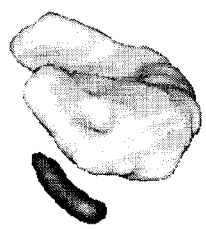
Figure 3A:
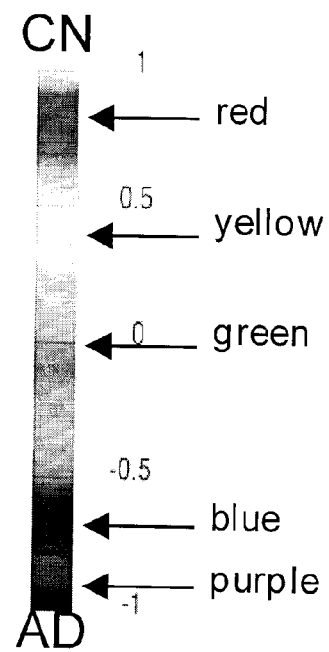
Figure 3B:
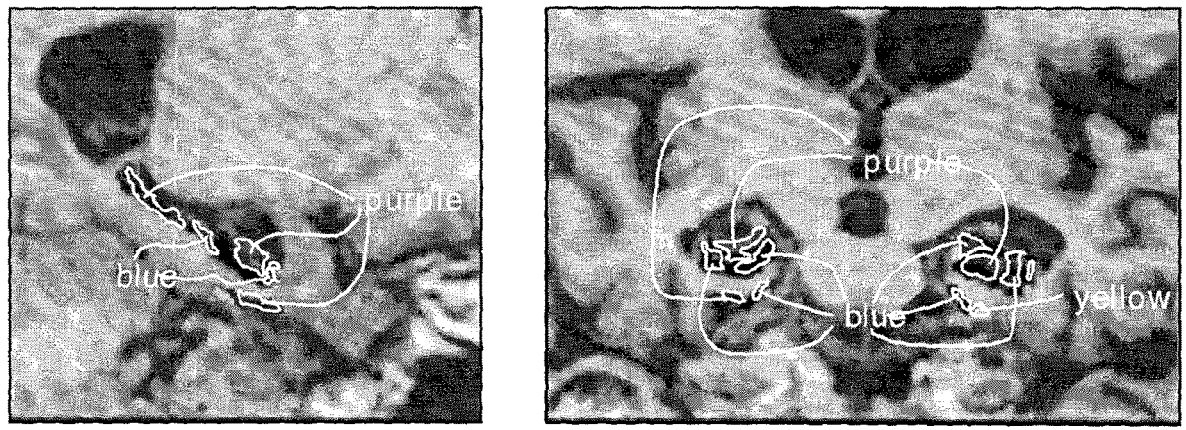
Figure 3B:
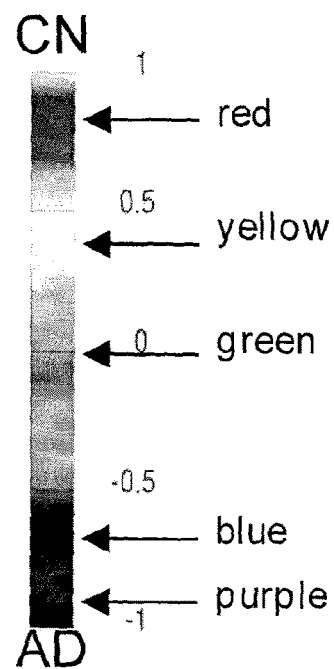

FIG. 2 shows an overview of the grading process where the N reference subjects closest to the subject's anatomy in the training library are equally selected from both populations. All these subjects have been subjected to automatic segmentations (although manual segmentation is also possible), resulting from the label propagation step, of the studied structures (the left HC segmentations are displayed in this example).

For each patch of the subject under study (patient with AD in this example), a comparison is performed with all the patches constituting the selected training subjects (some examples of similar patches are displayed). By this way, the simultaneous segmentation and grading of the studied structure is obtained. The final grading value corresponds to the average value over the estimated segmentation. This procedure is achieved for each studied structure: left and right HC and left and right EC.

Applicants extend this segmentation method to efficiently aggregate clinical state (e.g. CN or AD) in order to estimate the proximity (in the nonlocal means sense) of each voxel compared to both populations constituting the training library (see FIG. 2). To achieve this goal, applicants introduce the new concept of patch-based grading that reflects the similarity of the patch surrounding the voxel under study with all the patches present in the different training populations. In this way, the neighborhood information is used to robustly drive the search of anatomical patterns that are specific to a given subset of the training library. When the training populations include data from subsets of subjects in different clinical states, this approach provides an estimation of the grade (i.e., degree of closeness to one group or another) for each voxel:

$$g(x_i) = \frac{\sum_{s=1}^{N} \sum_{j \in \Omega} w(x_i, x_{s,j}) \cdot p_s}{\sum_{s=1}^{N} \sum_{j \in \Omega} w(x_i, x_{s,j})} \quad (4)$$

where $p_s$ is the clinical state of the training subject s. In applicants' case, $p_s = -1$ was used for AD state and $p_s = 1$ for CN state. A negative grading value (respectively, a positive grading value) $g(x_i)$ indicates that the neighborhood surrounding $x_i$ is more characteristic of AD than CN (respectively, of CN than AD) (see FIG. 3). The absolute value $|g(x_i)|$ provides the confidence given to the grade estimation. When $|g(x_i)|$ is close to zero, the method indicates that the patch under study is similarly present in both populations and thus is not specific to one of the compared populations and provides little discriminatory information. When $|g(x_i)|$ is close to 1, the method detects a high proximity of the patch under study with the patches present in one of the training populations and not in the other. Finally, for each subject, an average grading value is computed over all voxels in the estimated structure segmentation (e.g., for all $x_i$ with $v(x_i) \geq 0.5$) for each side (e.g., $\bar{g}_{HC-left}$ or $\bar{g}_{EC-right}$). Since the grading and the segmentation involve the same patch comparison step, these structures are extracted at the same time that their grade is estimated (see FIG. 3).

Several strategies can be used to fuse the average grading of the studied structures. First, each side of the structure can be used separately. Second, it is possible to assign the same weight to the left and right HC and EC (e.g., $\bar{g}_{HC} = (\bar{g}_{HC-left} + \bar{g}_{HC-right})/2$). This strategy of fusing both sides appears to be more robust to segmentation inaccuracy when compared to Chupin et al. [Chupin, M., Gerardin, E., Cuingnet, R., Boutet, C., Lemieux, L., Lehericy, S., Benali, H., Garnero, L., Colliot, O., 2009a. Fully automatic hippocampus segmentation and classification in Alzheimer's disease and mild cognitive impairment applied on data from ADNI. Hippocampus 19, 579-587]. During experiments, applicants found that these two strategies provided similar results for HC and EC. However, for the HC–EC complex, the best strategy was to compute left and right average grading values over HC–EC segmentation (this giving more importance to HC because of its larger size) and then to use the mean of both sides ($\bar{g}_{HCEC} = (\bar{g}_{HCEC-left} + \bar{g}_{HCEC-right})/2$). Therefore, applicants decided to present all the results using the second strategy.

Training library construction. Datasets: the publically available ADNI database (www.loni.ucla.edu/ADNI) was used to validate the proposed approach. This database contains both 1.5T and 3.0T T1-w MRI scans. For applicants' experiments, applicants randomly selected 120 MRI scans, 60 1.5T MRI baseline scans of CN subjects and 60 1.5T MRI baseline scans of patients with AD.

Preprocessing: All the selected images were preprocessed as follows: 1) correction of inhomogeneities using N3 taught by Sled et al in 1998 [Sled, J. G., Zijdenbos, A. P., Evans, A. C., 1998. A nonparametric method for automatic correction of intensity nonuniformity in MRI data. IEEE Trans. Med. Imaging 17, 87-97], 2) registration to the stereotaxic space using a linear transform to the ICBM152 template ($1\times1\times1$ mm$^3$ voxel size) taught by Collins et al. in 1994 [Collins, D. L., Neelin, P., Peters, T. M., Evans, A. C., 1994. Automatic 3D intersubject registration of MR volumetric data in standardized Talairach space. J. Comput. Assist. Tomogr. 18, 192-205], and 3) cross-normalization of the MRI intensity using the method proposed in Nyul [Nyul, L. G., Udupa, J. K., 2000. Standardizing the MR image intensity scales: making MR intensities have tissue specific meaning. Medical Imaging 2000: Image Display and Visualization 1, 496-504]. After preprocessing, all the MRIs are coarsely aligned (linear registration), tissue intensities are homogeneous within each MRI volume (inhomogeneity correction) and across the training database (intensity normalization).

Label propagation: From the 120 processed MRI scans, 20 scans (10 CN and 10 AD) were randomly selected to be used as seed dataset for segmentation. The HC and the EC of this seed dataset were manually segmented by following the protocol defined in Pruessner et al. [Pruessner, J. C., Kohler, S., Crane, J., Pruessner, M., Lord, C., Byrne, A., Kabani, N., Collins, D. L., Evans, A. C., 2002. Volumetry of temporopolar, perirhinal, entorhinal and parahippocampal cortex from high-resolution MR images: considering the variability of the collateral sulcus. Cereb Cortex 12, 1342-1353]. The manual segmentations of the seed dataset were then propagated to the 100 remaining scans constituting applicants' test dataset using the method described in (Coupé et al., 2011b). After the segmentation propagation step, the test dataset was composed of 100 MRI (50 CN subjects and 50 patients with AD) with their corresponding automatic segmentations (see FIG. 2). In applicants' test dataset, the average age of the populations is 74.8 (±4.8) for CN and 74.9 (±6.4) for AD. The age for the two populations is not significantly different (p=0.36, unpaired t-test). In addition, the Mini Mental State Evaluation (MMSE) is 29.1 (±1.2) for CN and 23.2 (±2.0) for AD.

Implementation details. In all experiments described here, the optimal parameters empirically found in Coupé et al. (2011b) for HC segmentation have been used and thus the patch size was fixed to 7×7×7 voxels and the pre-selection threshold set to th=0.95.

As done in Coupé et al. (2011b), $\Omega$ was replaced by a cubic volume $V_i$ centered on $x_i$. First, this strategy to use a semi-local paradigm instead of a fully nonlocal paradigm makes the processing computationally practical. In the denoising literature, this approach is used in the majority of the papers and has been shown to produce near-optimal or optimal results except for images with repetitive textures. Second, as shown in Coupé et al. (2011b), in the case of HC segmentation, limitation of the search window provides better results (see left of FIG. 8 in Coupé et al. (2011b)). Since all the images are linearly registered, the patches belonging to HC are located within a restricted area. By using a larger search window, outliers are added that marginally degrade the segmentation and uselessly increases the computational time. While in Coupé et al. (2011b) the search window size was fixed, applicants used a locally adaptive search window size. The initialization of the search window was set to 9×9×9 voxels as suggested in Coupé et al. (2011b). However, in the case when no similar patches can be found in this search window (i.e., none of the patches pass through the pre-selection), its radius is increased by one voxel until at least one similar patch in each population is found (i.e., at least one patch in each population pass through the pre-selection step). For all the studied subjects, the largest search window size found was 15×15×15 voxels.

The automatic local adaptation of the smoothing parameter $h^2(x_i)$ (see Eq. 1) proposed in Coupé et al. (2011b) has been slightly modified. During all the experiments, the squared smoothing parameter was set proportional (with $\lambda=0.5$) to the minimal SSD:

$$h^2(x_i) = \lambda^2 \times \underset{x_{s,j}}{\mathrm{argmin}} \; \|P(x_i) - P(x_{s,j})\|_2^2 + \varepsilon \qquad (5)$$

The value of lambda slightly changes the segmentation results. When applicants validated their segmentation method on the ADNI dataset in Coupé et al. [Coupé, P., Fonov, V., Eskildsen, S., Manjon, J., Arnold, D., Collins, L., 2011a. Influence of the training library composition on a patch-based label fusion method: Application to hippocampus segmentation on the ADNI dataset. Alzheimer's and Dementia 7, S24-S24], using $\lambda=0.5$ instead of $\lambda=1$ changed the median Dice-Kappa values from 0.882 to 0.883 for CN and from 0.836 to 0.838 for AD.

Finally, a subject selection was also applied to reduce the number of training MRI required. For each structure, the N closest subjects (in terms of SSD over the initialization mask as done in Coupé et al. (2011b)) are equally selected from both populations (N/2 from the CN population and N/2 from the AD population) (see FIG. 2). This is done to ensure that the size of the "patch pool" from the AD population is coarsely similar to the size of the "patch pool" from the CN population.

For a given subject with N=20 (i.e., 10 AD training templates and 10 CN training templates), the segmentation and the grading maps were obtained in less than 4 minutes for left and right HC and less than 2 minutes for left and right EC using a single core of an Intel Core 2 Quad Q6700 processor at 2.66 GHz.

Validation Framework.

Applicants' validation framework was designed to compare the capability of different biomarkers to discriminate between patients and controls. The biomarkers studied were: HC volume, HC grade, EC volume and EC grade as well as their combination.

First, to obtain the segmentation and the grade of the subjects within the test dataset, a leave-one-out procedure was performed over the 100 subjects using their corresponding automatic segmentations resulting from the label propagation step (see FIG. 2). For each subject, the N closest training subjects were selected from the 99 remaining subjects in the library. The average grading value was then estimated over the EC and the HC segmentations (for both left and right sides) obtained at the same time (see an example in FIG. 3). These segmentations were also used to measure the HC and EC volumes in the stereotaxic space.

Once all the subjects had a volume and a grade for each structure, a quadratic discriminant analysis (QDA) was performed. Each subject was classified by performing a QDA over the 99 remaining subjects. This approach was applied to volume-based classification, grade-based classification and the combination of both for HC, EC and HC+EC. Applicants found that QDA slightly improved the results compared to linear discriminant analysis, especially when the subject's age was used as an additional parameter. The success rate (SR), the specificity (SPE), the sensitivity (SEN), the positive predictive value (PPV) and negative predictive value (NPV) are presented for each of the tested biomarkers, as taught in Cuingnet et al. [Cuingnet, R., Gerardin, E., Tessieras, J., Auzias, G., Lehericy, S., Habert, M. O., Chupin, M., Benali, H., Colliot, O., 2010. Automatic classification of patients with Alzheimer's disease from structural MRI: A comparison of ten methods using the ADNI database. Neuroimage].

FIG. 3 shows the grading maps obtained for 2 test subjects (1 CN and 1 AD) overlaid with a color scale from −1 (AD) to +1 (CN) The image slices of both subjects (3a and 3b) have the same position in stereotaxic space. The volumes in stereotaxic space and the average grade values for each structure are provided in the figure. For each subject, 3D renderings of the segmentations are presented. The colour scale as shown in Coupé et al. 2012 [Coupé, P., Eskildsen, S. F., Manjon, J. V., Fonov, V. S., Collins, D. L.: Simultaneous segmentation and grading of anatomical structures for patient's classification: application to Alzheimer's disease. Neuroimage 59, 3736-3747 (2012)] but shown in grayscale for this document, runs from black (at −1.0) to blue to cyan to green (at 0.0) to yellow, orange, red and finally white (at +1.0). The corresponding average grading values and the estimated volumes are also provided for left and right HC and for left and right EC. Visually, the CN subject clearly appears closer to the CN population (mainly red color related to values close to 1) while the AD patient is visually closer to the AD population (mainly purple and black colors related to values close to −1). In addition, FIG. 3 also provides a visual assessment of the quality of the segmentation and grading.

Volumetric Study.

Figure 4A:
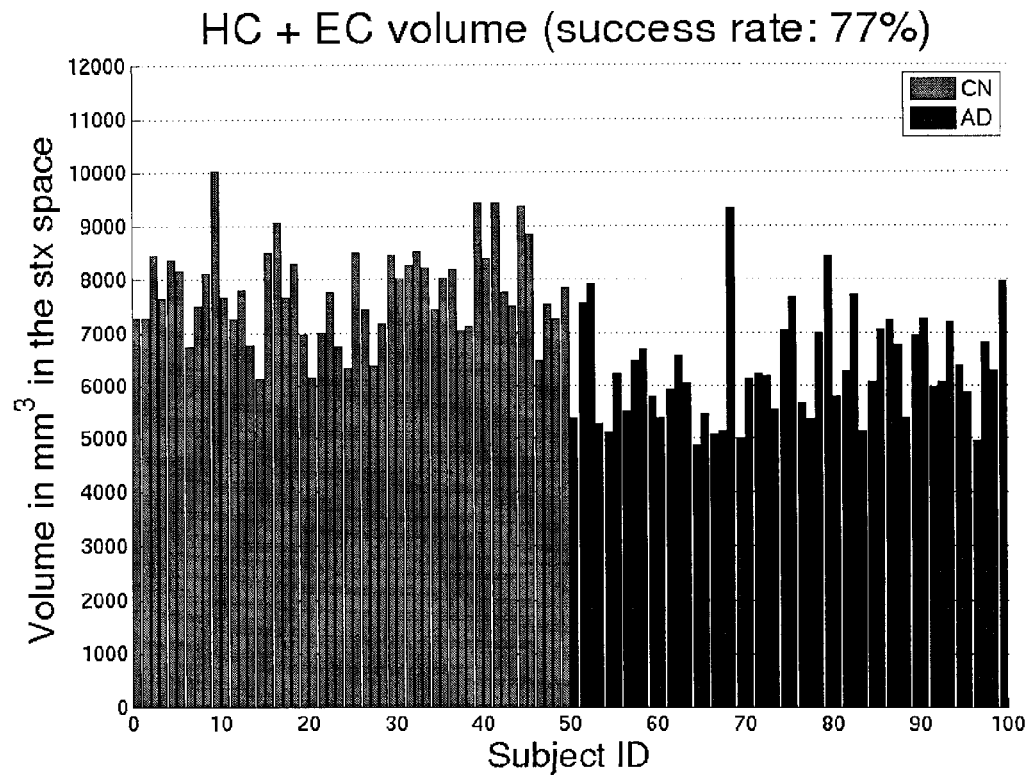
FIG. 4 shows volume (FIG. 4A) and grading (FIG. 4B) values for 100 subjects for the combination of HC and EC structures studied.
Figure 4B:
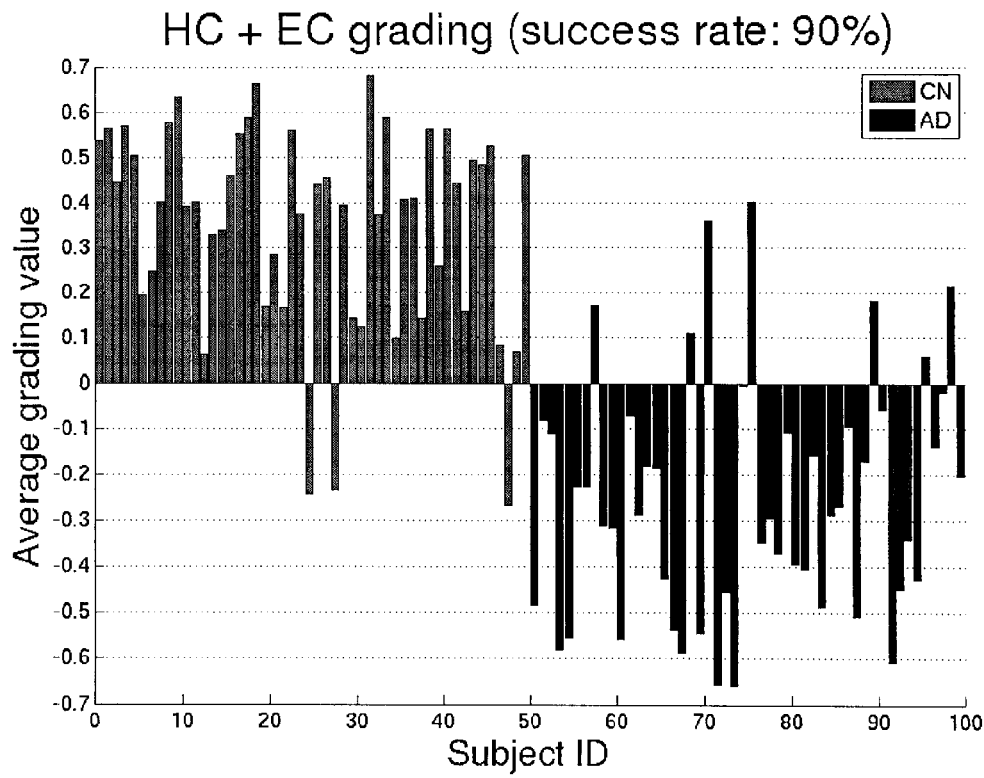

The left column of FIG. 4 shows the volumes for the 100 subjects of the test dataset for HC and EC for a training library of size N=100 (i.e., 50 CN and 50 AD). The volumetric approach provided a classification success rate of 80% for HC and 69% for EC. The use of both structures at the same time produced a success rate of 78% through applicants' QDA-based classification. This result indicates that the estimated HC volume is more powerful than the EC volume to identify patients with AD. This observation is in accordance with Frisoni et al. (1999). Applicants' result using only HC volume is slightly superior to a recently published method comparison (Cuingnet et al., 2010). This might come from differences in the test dataset used here or due to a higher accuracy and consistency of the segmentation method used compared to Chupin et al. (2009b). The success rate obtained with EC volume is similar to the results reported in Frisoni et al. (1999) but lower than the values reported in other studies using manual segmentations. FIG. 4 shows the higher variability of EC volume compared to HC volume. As mentioned in the introduction, this range of volumes comes from the high inter-subject variability of EC, but may also be due to the difficulty to distinguish EC structure boundaries on anatomical MRI (e.g., identification of the collateral sulcus and the sulcus semiannularis). Due to this last point, less accurate segmentations may be obtained for this structure and thus the introduction of segmentation errors may negatively impact the patient's classification. The use of both structures at the same time did not improve the result compared to the method based on HC only, while improvements have been observed by other groups doing similar experiments on manual segmentations.

Grading Study.

FIG. 4 shows volumes and grading values of the studied structures for the 100 subjects tested (with template library N=80). The first fifty subject (subject ID=1 to 50 represent the control normal (CN) aging subjects and are represented in light gray bars. The second fifty subjects (subject ID from 51 to 100) represent the subjects with Alzheimer's disease (AD) and are represented in dark grey bars. The success rates are obtained using quadratic discriminant analysis (QDA) between both populations in a leave-one-out fashion. As shown in FIG. 4, the success rate of the classification was 90% using HC+EC grading as compared to 77% using HC+EC volume. When using only EC, the success rate was 78% with grading and 69% with volume while for HC, the success rate was 89% with grading and 80% with volume (not shown). For HC, the success rate obtained by using QDA is similar to thresholding the grading value at zero (4 false positives CN and 7 false negatives AD). In fact, in the perfect case, the 50 first subjects (CN) should have positive average grading values and the 50 last (AD) should have negative average grading values. This result indicates that the HC grade estimator is not biased and thus that the sign of the final grading value can be used directly to classify the patient. On the other hand, the EC grade estimator is biased in the sense that the optimal threshold obtained using QDA is superior to zero. The EC grades of AD are frequently superior to zero, thus indicating a higher similarity with the patches present in CN population. As applicants will show later, the normal age-related structural changes in the EC may disturb the detection of the disease-related anatomical changes. However, this bias, which depends on the training library used, can be partially compensated for by using QDA, yielding a success rate of 78%. Finally, by the computation of the average grade value over the HC and the EC improved the HC results and leads to a very high success rate of 90%.

Comparison of Anatomical Biomarkers.

In Tab. 2 below, the SEN, SPE, PPV and NPV obtained by the different biomarkers considered are presented. These results show that for both structures studied, the classification based on grading provides significantly better results than the volumetric approach (89% vs. 80% for HC and 78% vs. 69% for EC). Moreover, while the combination of HC+EC tends to spoil the results of volumetric analysis, the combination of both slightly improves the results of the grading study. Three different combinations of biomarkers obtained a success rate of 90% during applicants' experiments: HC volume and grade, HC+EC grade, HC+EC volume and grade. In the three cases, the HC grading was used, indicating a potential key role of this new imaging biomarker.

TABLE 2

Results of the patient classification (AD vs CN) for the different biomarkers under investigation. These results were obtained by using discriminant analysis through a leave-one-out procedure on the test dataset with N = 80 (i.e., 40 CN and 40 AD).

| AD vs. CN | SR | SEN | SPE | PPV | NPV |
|---|---|---|---|---|---|
| HC volume | 80% | 78% | 82% | 81% | 79% |
| HC gracing | 89% | 86% | 92% | 91% | 87% |
| HC volume and grading | 90% | 88% | 92% | 92% | 88% |
| EC volume | 69% | 66% | 72% | 70% | 68% |
| EC grading | 78% | 74% | 82% | 80% | 76% |
| EC volume and grading | 78% | 74% | 82% | 80% | 76% |
| HC + EC volume | 78% | 76% | 80% | 79% | 77% |

TABLE 2-continued

Results of the patient classification (AD vs CN) for the different biomarkers under investigation. These results were obtained by using discriminant analysis through a leave-one-out procedure on the test dataset with N = 80 (i.e., 40 CN and 40 AD).

| AD vs. CN | SR | SEN | SPE | PPV | NPV |
|---|---|---|---|---|---|
| HC + EC grading | 90% | 86% | 94% | 93% | 87% |
| HC + EC volume and grading | 90% | 88% | 92% | 92% | 88% |

Impact of the Number of Selected Best Training Subjects.

Figure 5A:
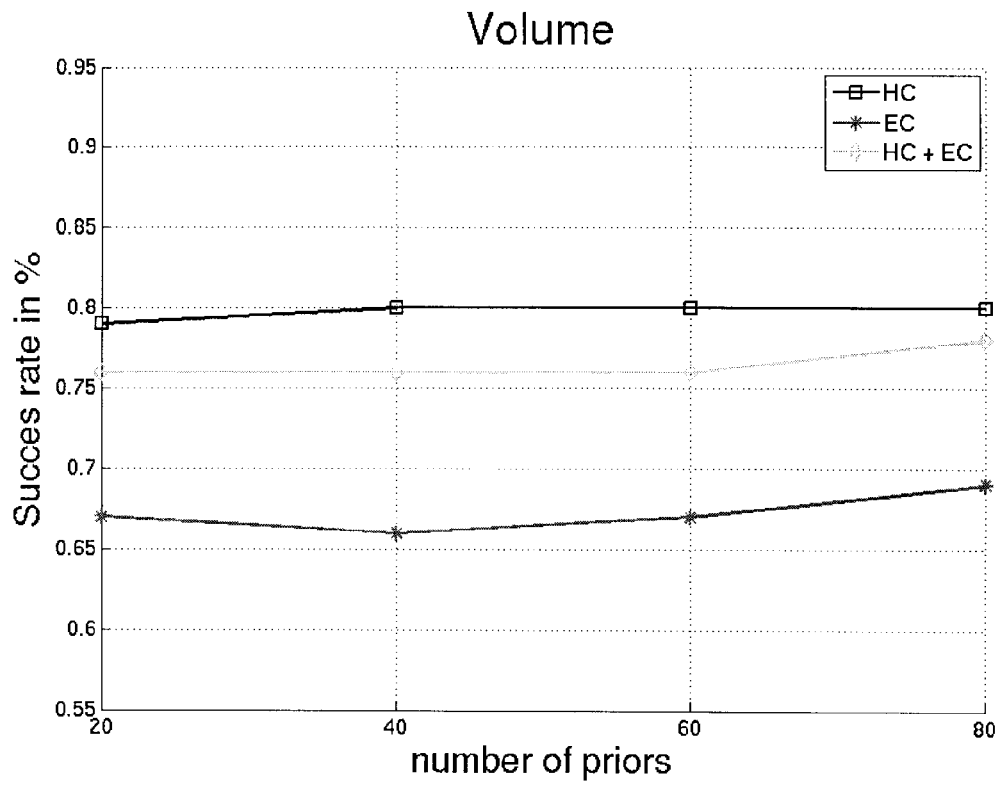
FIG. 5 shows the impact of the number of reference images used as priors as well as the contribution of age to the success rate of state determination for volume (FIG. 5A), Volume+Age (FIG. 5B), Grade (FIG. 5C), Grade+Age (FIG. 5D) and volume and grade (FIG. 5E), Volume and Grade+Age (FIG. 5F).
Figure 5B:
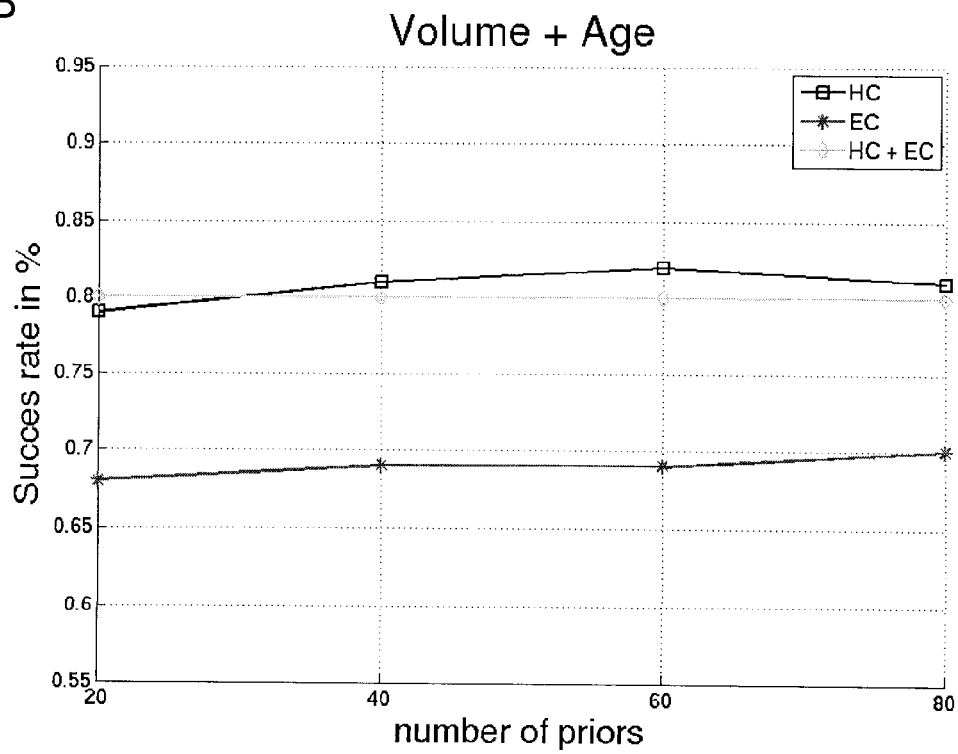
Figure 5C:
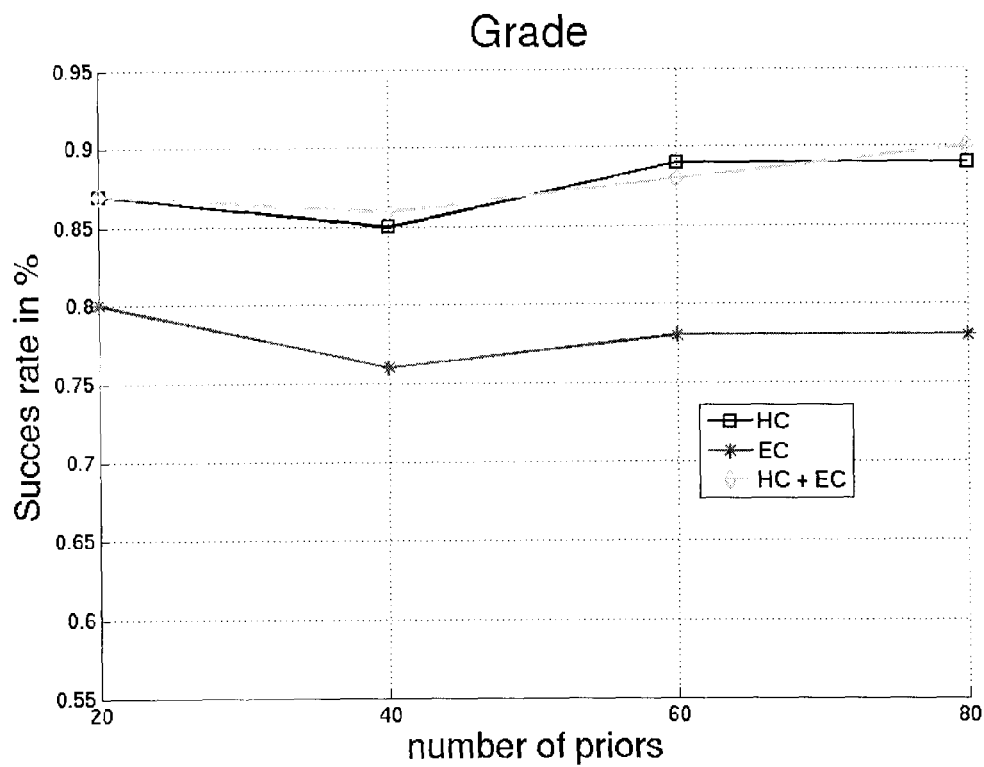
Figure 5D:
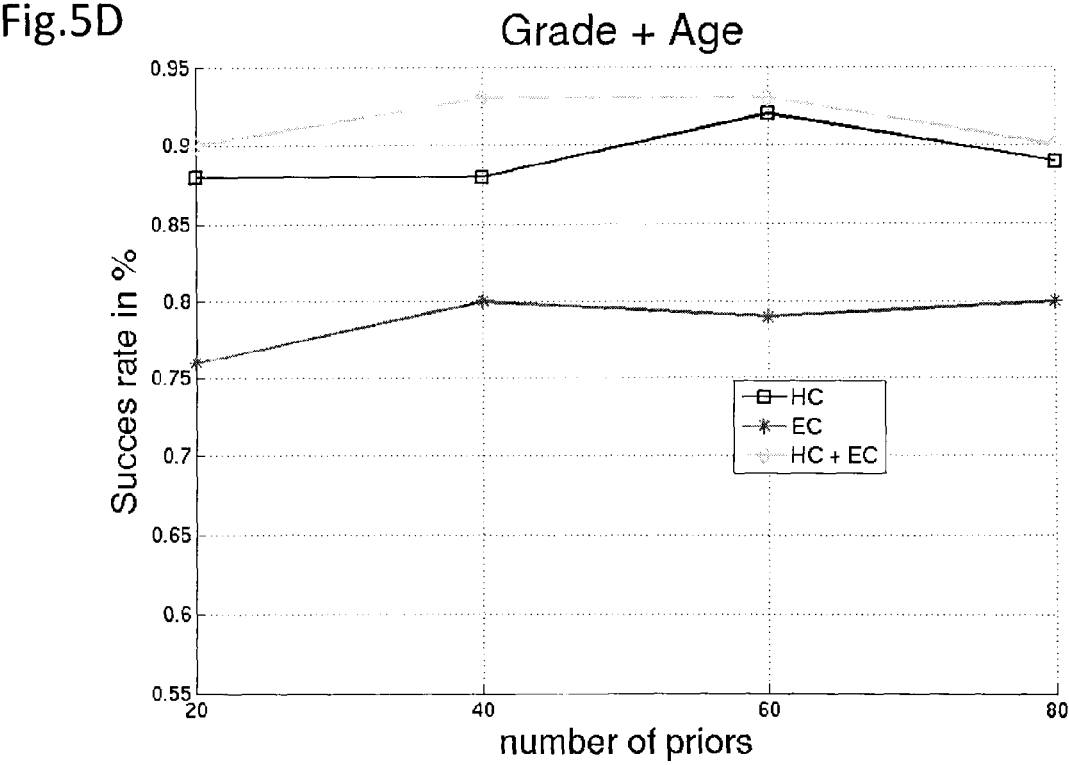
Figure 5E:
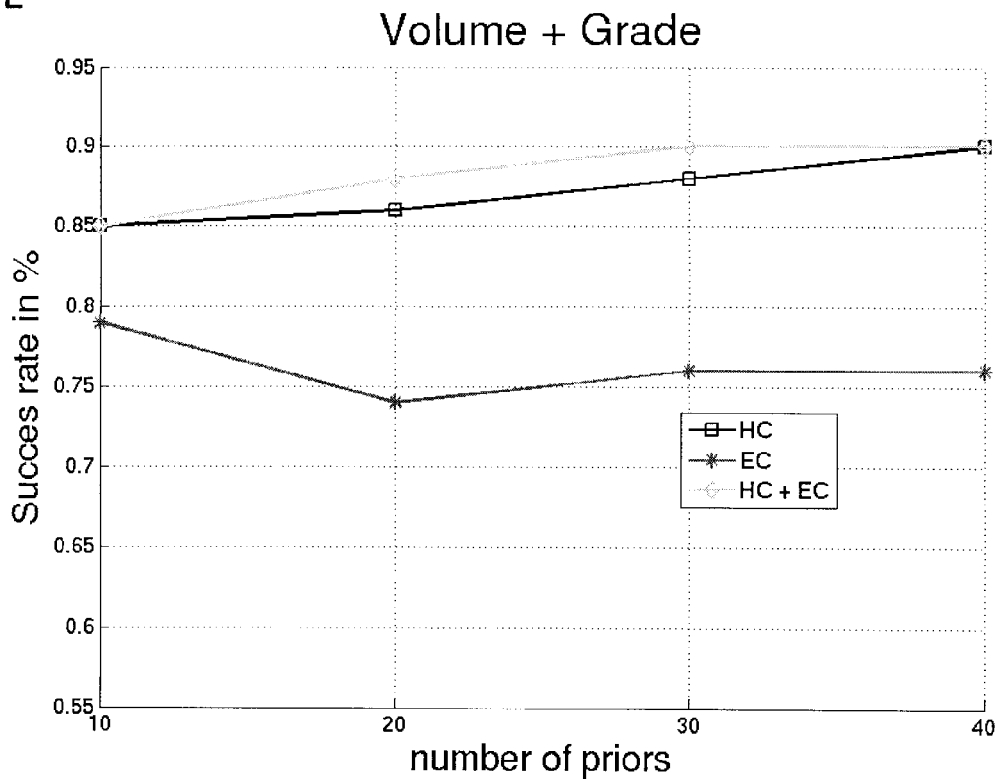
Figure 5F:
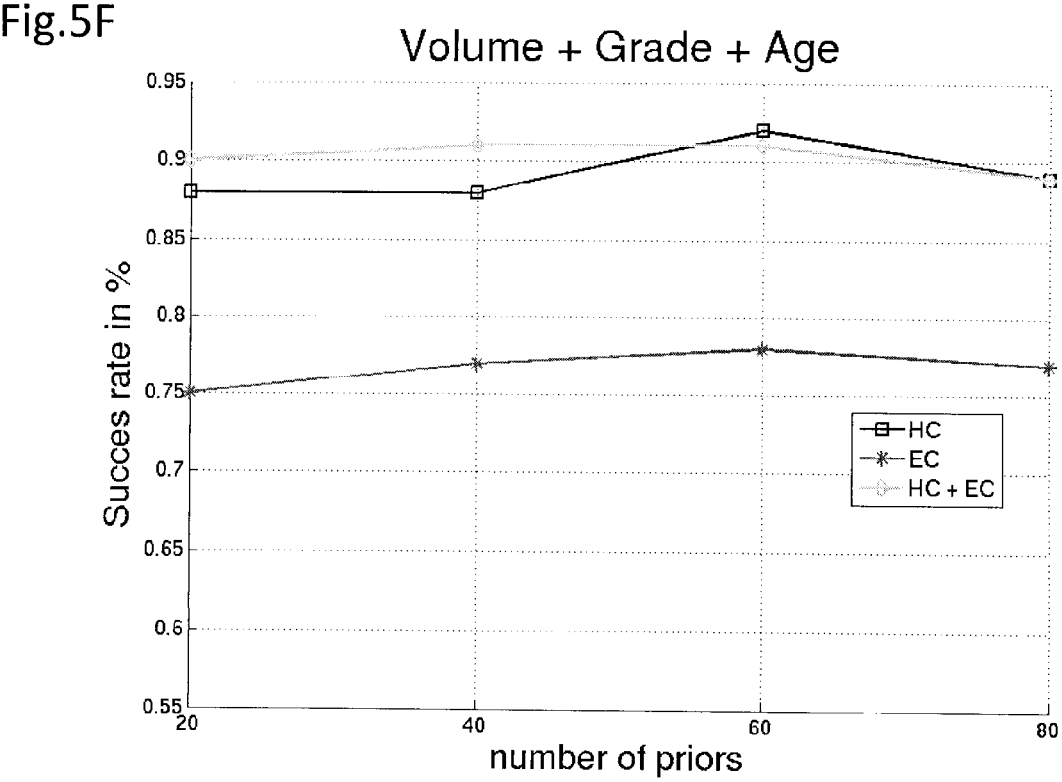

FIG. 5 shows the impact of the number of reference images used as priors as well as the contribution of age to the success rate of state determination for volume (FIG. 5A), Volume+Age (FIG. 5B), Grade (FIG. 5C), Grade+Age (FIG. 5D) and volume and grade (FIG. 5E), Volume and Grade+Age (FIG. 5F). Hippocampus (HC) is represented with square box symbols, the entorhinal cortex (EC) is represented with star symbols and their combination (HC+EC) is represented by small circles. The success rates are obtained using quadratic discriminant analysis (QDA) between both populations in a leave-one-out fashion. The success rate for all the biomarkers from N=20 (10 CN and 10 AD) to N=80 (40 CN and 40 AD). Applicants used the subject's age as supplementary information during QDA in order to increase classification accuracy.

Volume (FIGS. 5A and 5B): For HC, the classification accuracy was quite stable from N=40 to N=80. In Coupé et al (2011b), applicants showed that a plateau in terms of segmentation accuracy was reached around N=30. For EC, the best results were obtained for N=80. This result seems to indicate that a large library is required to achieve consistent segmentation of EC. Indeed, increasing the size of the "patch pool" and better address issues related to inter-subject variability. The addition of the age as parameter in QDA improved the results of the classification, especially for EC and HC+EC biomarkers. By performing the QDA only with age provided a success rate of 48% in the classification. Finally, at N=60, the HC volume combined with the age provided a success rate of 82%.

Grade (FIGS. 5C and 5D): For HC, the best classifications were obtained by using high N values (N=60 and N=80). For EC, the best classification rate was obtained for the smallest value of N=20, a result that was not expected. However, by also using age, the best results were obtained for N=80 for EC. For HC and for HC+EC based classifications, the inclusion of age improved the results of the classification. In these cases, HC-based classification yielded a success rate of 92% and HC+EC a success rate of 93% at N=40 and N=60.

Volume+Grade (FIGS. 5E and 5F): By combining the volume and the grade of the biomarkers, applicants obtained slightly better results than by using only the grade, except for EC. By using the age of the subjects, the volume and the grade over HC (with N=60) provided 92% classification accuracy. The combination of all the parameters (i.e., volume, grade and age) slightly decreased the results for the biomarkers involving EC compared to the use of only grade and age.

Relationship Between Grade and Age.

Figure 6A:
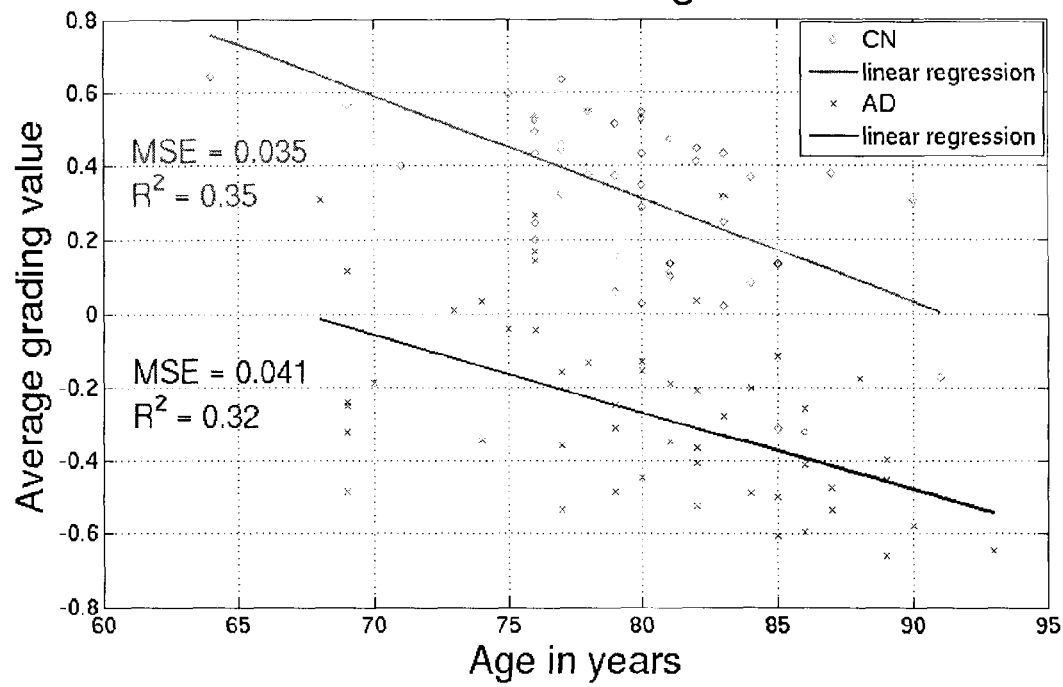
FIG. 6 shows the average grading value of control and AD patient images as a function of age in years using linear regression (FIG. 6A) and quadratic regression (FIG. 6B).
Figure 6B:
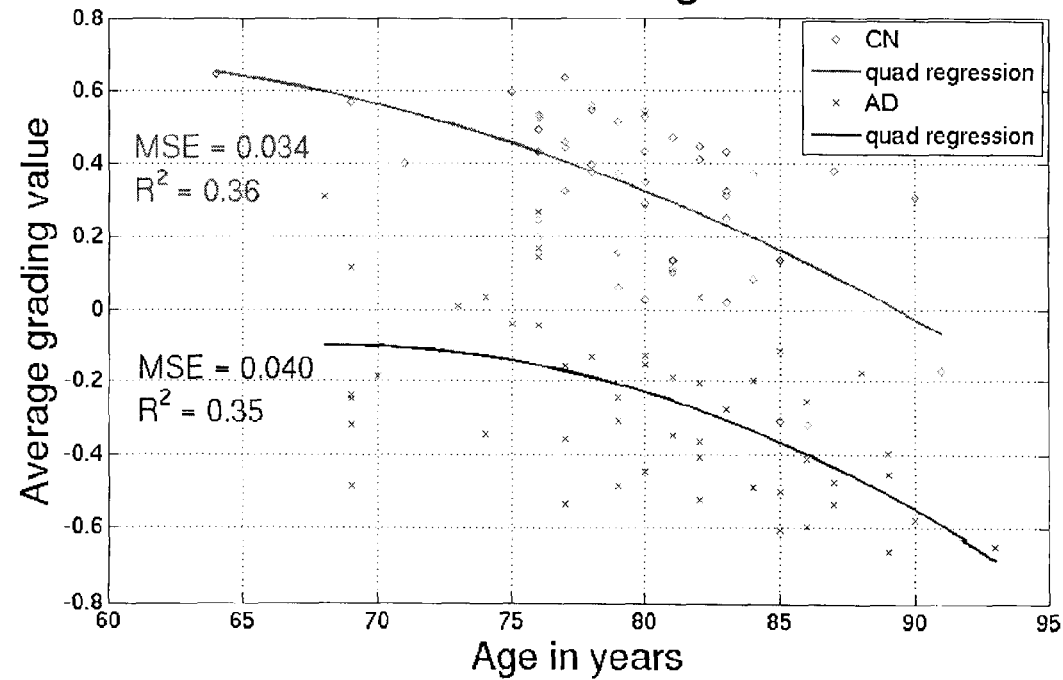
Figure 7A:
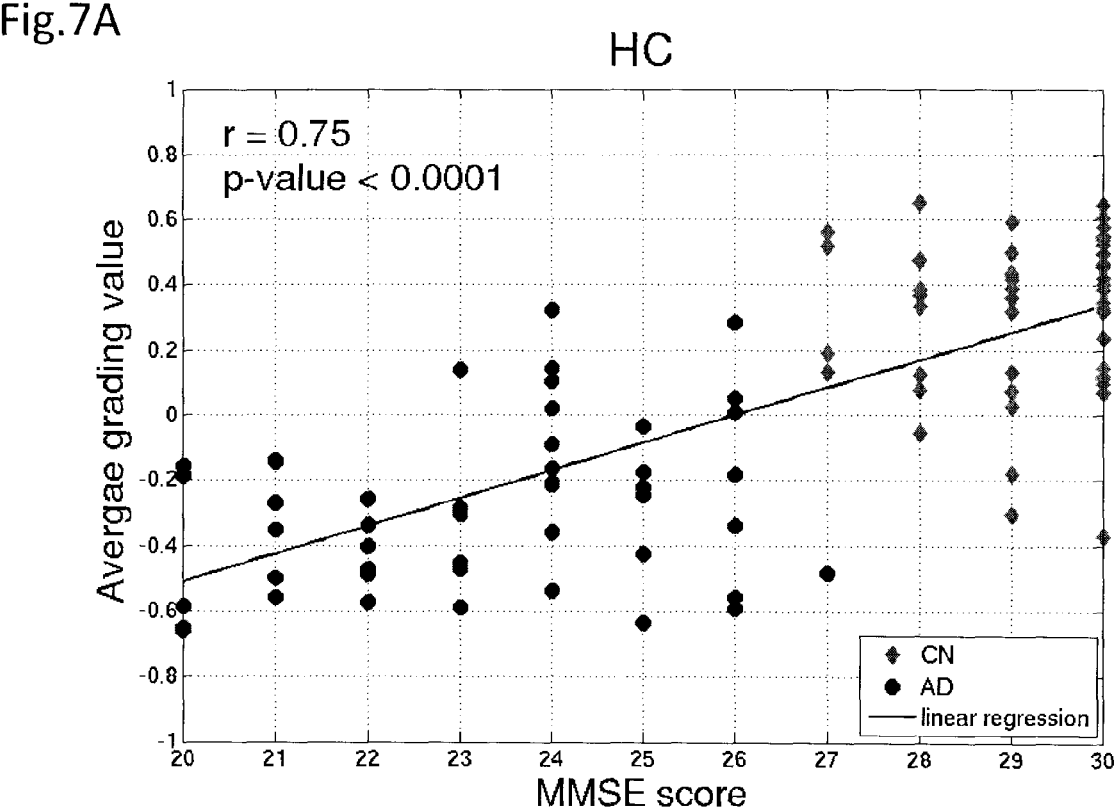
FIG. 7 is a graph showing the average grading (FIG. 7A HC and FIG. 7C EC) and volume (FIG. 7B HC and FIG. 7D EC) values of control and AD patient images as a function of the mini mental status exam (MMSE).
Figure 7B:
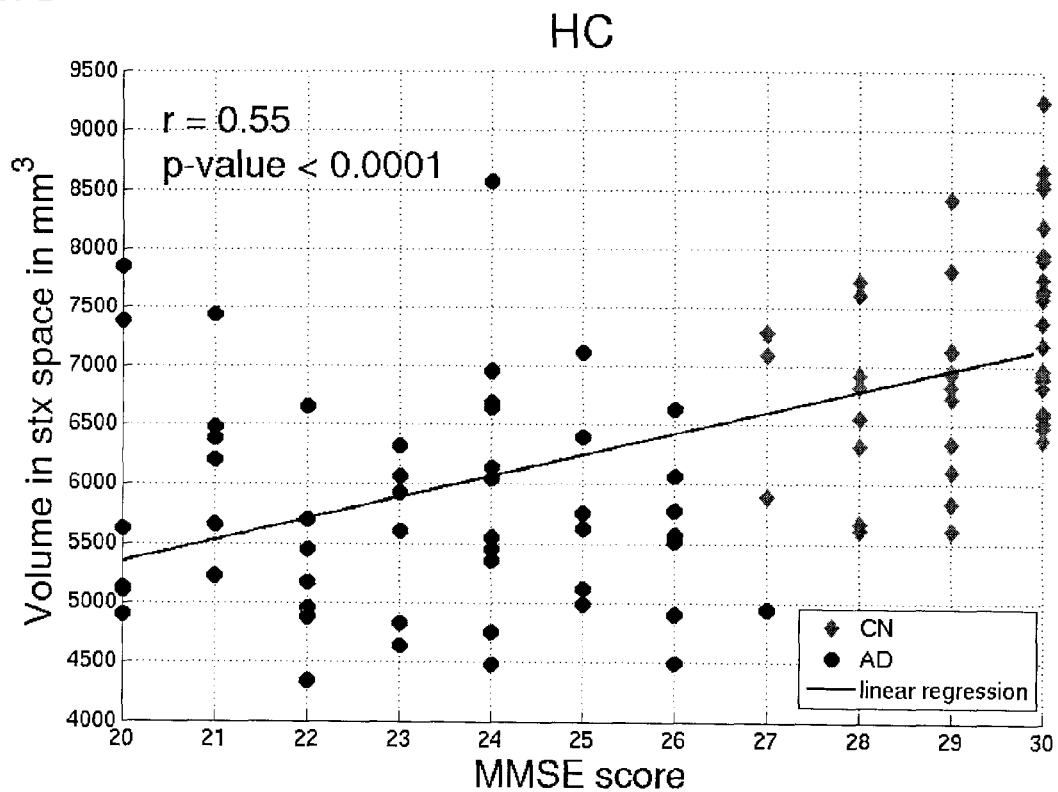
Figure 7C:
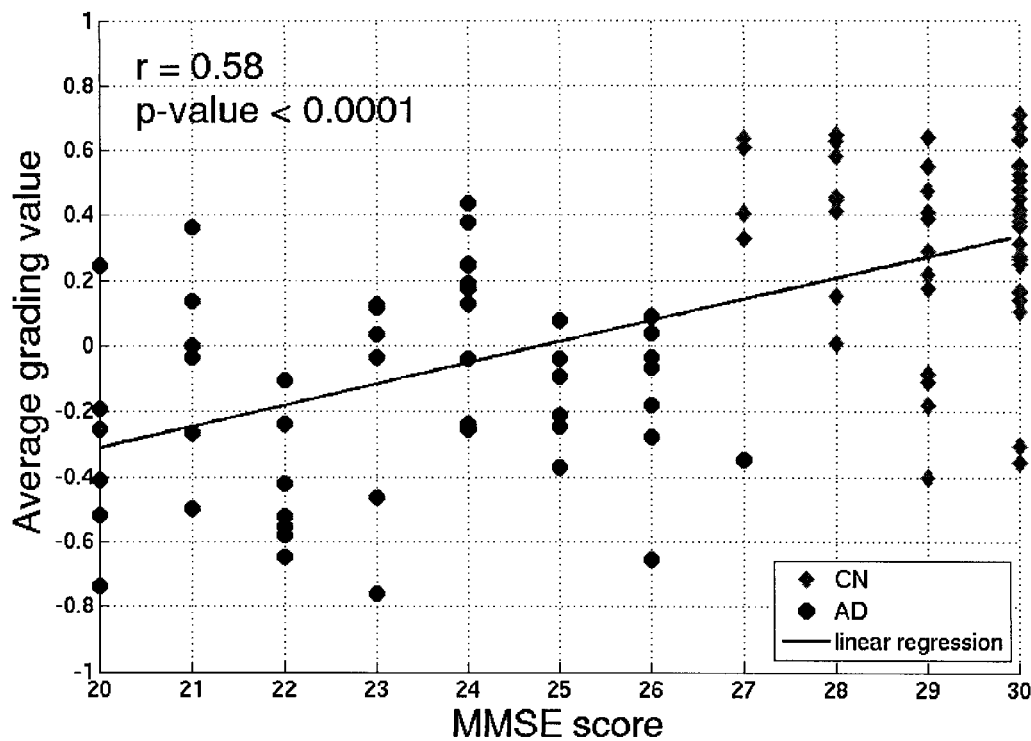
Figure 7D:
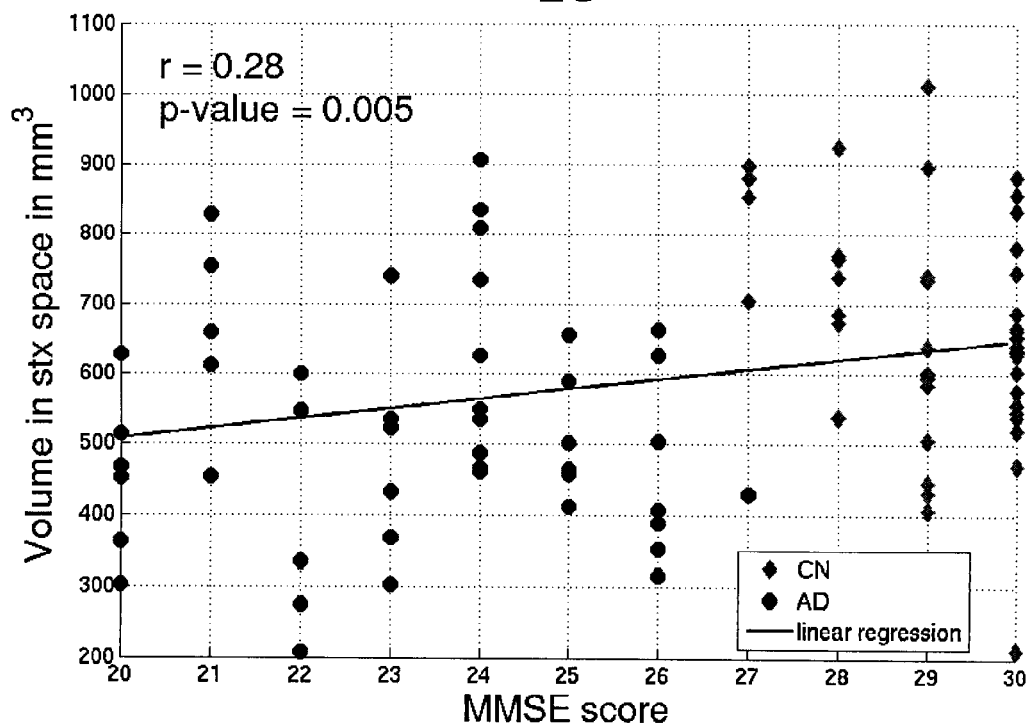

As shown in the FIG. 5, using the subject's age improved the classification based on the grading measure, except for EC with N=20. This supplementary information seems to help distinguish age-related MRI changes from those related to AD pathology. FIG. 6 shows control normal (CN) aging subjects are represented with open diamond symbols. Alzheimer's disease (AD) subjects are represented with small 'x's. The displayed grading values are obtained using HC+EC with N=60. We compared linear and quadratic fitting for both populations. FIG. 6 shows the grade values as a function of age on HC+EC with N=60 (the case with the highest classification accuracy: 93%) using linear regression (FIG. 6A) and quadratic regression (FIG. 6B). It appears that the grading values decrease with age in both populations. This variation indicates that the grading measure captures the age-related anatomical changes (possibly related to atrophy), and thus this observation may explain the better results obtained using age for all the biomarkers except for EC with N=20. As previously mentioned, QDA provides slightly better results than LDA during classification (between 0 to 2% depending on the biomarker studied). This slightly better fitting is assessed by Pearson's coefficient and corresponding p-value of the linear and quadratic regressions presented in FIG. 6. While for CN, the traditional linear model and quadratic regressions provided similar results, it seems that for AD a quadratic model fits better than a linear model. The nonlinear nature of the atrophy related to AD has recently been studied (Frisoni et al., 2010); and demonstrated that brain atrophy during AD is not a linear process while most studies assume a linear progression of AD. In addition, the grade measure is correlated with age while the volume does not appear to be statistically correlated with age since similar regressions provided correlation of $r=0.31$ for CN and $r=0.34$ for AD with respective p-values of 0.09 and 0.06.

Relationship Between Grade and MMSE Score.

Finally, the link between the mini mental state examination (MMSE) score and the grade is studied. The MMSE is a test evaluating the cognitive function of the patient. A useful imaging biomarker should have a link with the cognitive decline of the patient with AD usually estimated by using MMSE. Several studies have investigated the relationship between the MMSE score and the volume or the shape of key structures and EC. Applicants investigated the correlation between MMSE score and anatomical measurements (i.e., volume and grade) for HC and EC. FIG. 7 shows the plots of the grade and the volume as functions of the MMSE score. For both structures, the coefficient of correlation for grade was higher ($r=0.75$ for HC FIG. 7A and $r=0.58$ for EC FIG. 7C) than for the volume ($r=0.55$ for HC FIG. 7B and $r=0.28$ for EC FIG. 7D). A statistically significant correlation has been found in all cases. Another trend was that the HC measurements were more consistent with MMSE scores than EC measurements (see FIG. 7). Finally, the HC grade was the biomarker most consistent with MMSE with a high coefficient of correlation ($r=0.75$).

In Du et al. [Du, A. T., Schuff, N., Amend, D., Laakso, M. P., Hsu, Y. Y., Jagust, W. J., Yaffe, K., Kramer, J. H., Reed, B., Norman, D., Chui, H. C., Weiner, M. W., 2001. Magnetic resonance imaging of the entorhinal cortex and hippocampus in mild cognitive impairment and Alzheimer's disease. J Neurol Neurosurg Psychiatry 71, 441-447], the authors obtained a correlation coefficient of $r=0.48$ for HC and $r=0.48$ for EC volume based on manual segmentations with a p-value less than 0.001 in both cases. In applicants' experiment, slightly higher correlation was obtained for HC, but a significantly lower value was obtained for EC as assessed by a higher p-value=0.005. However, applicants' correlation coefficient between EC volume and MMSE score is $r=0.34$. It should be noted that the estimation of correlation on discrete functions such as MMSE can bias the significance of correlation. However, applicants wanted to compare applicants' results with previously published studies using this metric.

During experiments, applicants showed that: i) HC-based measures were more discriminant than EC-based measures, ii) the grading had a higher discriminatory capability than the volume, by adding the age, the classification rate improved, especially when using the HC-grade-based metrics, iv) by computing the grade over a larger area (HC+EC) tended to slightly improve results, especially when the subjects' ages were used within the classification model, and v) the optimal size of the number of selected training subjects were N=60 (60% of the full library) in the majority of the situations studied. A balance appears to be required between using a large enough training population and potentially introducing outlier subjects by using all the available subjects. According to the structure of interest, a different number of training subjects could be used. Moreover, by using a larger library, it could be possible to select a higher number of subjects without introduction of outliers. The difficult segmentation of EC due to inter-subject variability could be partially compensated by using non-linear registration of training subjects instead of linear registration. However, this type of approach is more computational intensive. The introduction of shape priors could also be a possibility to deal with ambiguity of the EC boundaries.

The SEN, SPE, PPV and NPV obtained by applicants' grading approach are competitive compared to the ten methods compared in Cuingnet et al. (2010) involving voxel-based morphometry (VBM), cortical thickness, HC volume and HC shape (Gerardin et al., 2009). In that comparison paper, the best VBM-based approach obtained 89% accuracy; the best method based on cortical thickness obtained 85% accuracy, the best approach using HC volume 74% accuracy and the method using HC shape 77% accuracy. However, during applicants' experiment, only a subset of the entire ADNI database has been used, contrary to the experiments done in (Cuingnet et al., 2010). Moreover, the classification algorithm used in Cuingnet et al. (2010) was a support vector machine while applicants used a quadratic discriminant analysis approach. Despite these differences, the classification results obtained by using grade only are competitive to the best results reported in Cuingnet et al. (2010). Moreover, by adding the subjects' age yielded an accuracy of 93%. This result is similar to the highest classification accuracy 93.3% reported on a similar sized subset of ADNI (51 AD and 52 CN) in Zhang et al. [Zhang, D., Wang, Y., Zhou, L., Yuan, H., Shen, D., 2011. Multimodal classification of Alzheimer's disease and mild cognitive impairment. Neuroimage 55, 856-867]. However, Zhang used a multimodal approach involving positron emission tomography (PET) and cerebro-spinal fluid (CSF) markers to reach this degree of accuracy. By using only MRI, their method based on volumetric features provided an accuracy of 86.2%.

It appears that using a larger area of analysis by grading several structures tended to improve the grading estimation. Investigating the spatial distribution of grade maps over predetermined populations as well as the extension of grading to other key structures impacted by AD, such as parahippocampal cortex and perihinal cortex or fornix and mammillary body could help improve AD detection and allow to reach determination thresholds of 80% compared to the 74% determination threshold, as shown herein, using HC grade. This information could help to detect more discriminant areas for classification and might provide information on the AD progression. Finally, the application of the proposed grading measure. The extension of grading to other key structures impacted by AD seems to be an interesting path to follow for further research. Structures such as parahippocampal cortex and perihinal cortex or fornix and mammillary body could be valuable anatomical structures to improve AD detection. Moreover, further work should investigate the spatial distribution of grade maps over the populations. This information could help to detect more discriminant areas for classification and might provide information on the AD progression. Finally, the application of the proposed grading measure to other diseases has a great potential. Moreover, the difficult problem of clinical differentiation (such as AD and frontal lobe dementia for instance) should also be investigated.

Using SSD as similarity metric, applicants' approach is sensitive to inaccuracy in inter-subject intensity normalization. In Coupé et al. (2011a; 2011b), applicants demonstrated that the proposed preprocessing pipeline involving (Nyul and Udupa, 2000) provides a sufficiently robust normalization to obtain accurate segmentations. In this paper, applicants also showed that the preprocessing pipeline used yields high classification accuracy. Nevertheless, any improvements on the inter-subject normalization should yield further improvements in grading estimation. The use of other similarity metrics less sensitive to intensity normalization should be studied in future work. However, according to applicants' experiments, there is no trivial solution since cross-correlation or correlation ratio cannot distinguish constant areas with different means (e.g, in CSF and white matter), mutual information requires a higher number of samples (bigger patch) and introduces the binning problem for histogram construction, and finally the SSIM index also requires matching of intensity. The use of hybrid metrics based on intensity and derivatives could be further investigated.

As for Voxel-Based Morphometry (VBM)-based approaches, applicants' method requires several scans of each population to be usable. The construction of a large enough training library might be an issue for trials based on a small number of subjects. However, the number of training subjects required by applicants' method is similar to the number required by VBM studies. A group size of 30 to 50 subjects per population is typical in a VBM study while a group size of 70-90 subjects per population is optimal for detection of HC volume loss. Applicants found that 30 subjects from each population is sufficient to provide very high classification rates.

In the proposed grading technique, applicants focused on the problem of AD vs. CN classification. However, the prediction of conversion from prodromal AD (one form of mild cognitive impairment) to clinically definite AD is more useful from a clinical and diagnostic point of view. The prediction of patients with MCI who will convert to AD and those who will stay stable is an extremely complex task for which no method has yet provided satisfactory classification results. Proposed methods based on structural MRI have been focusing on gray matter loss as markers for prediction. Applicants' proposed grading method adds valuable information for the problem of prediction.

The method proposed herein allows to robustly detect the patterns of anatomical change in the hippocampus and entorhinal cortex caused by AD. Applicants' method has the advantage of: i) simplicity (it can be coded in few hundred lines of code), ii) low computational cost (as it does not require non-rigid registration), iii) robustness of the process (all the subjects get final grading maps) and iv) the possibility to achieve individual classifications based on a MRI data from a single time point (contrary to group classifications or longitudinal studies). These results indicate that this new structure grading approach is a useful biomarker to efficiently detect AD.

Figure 8:
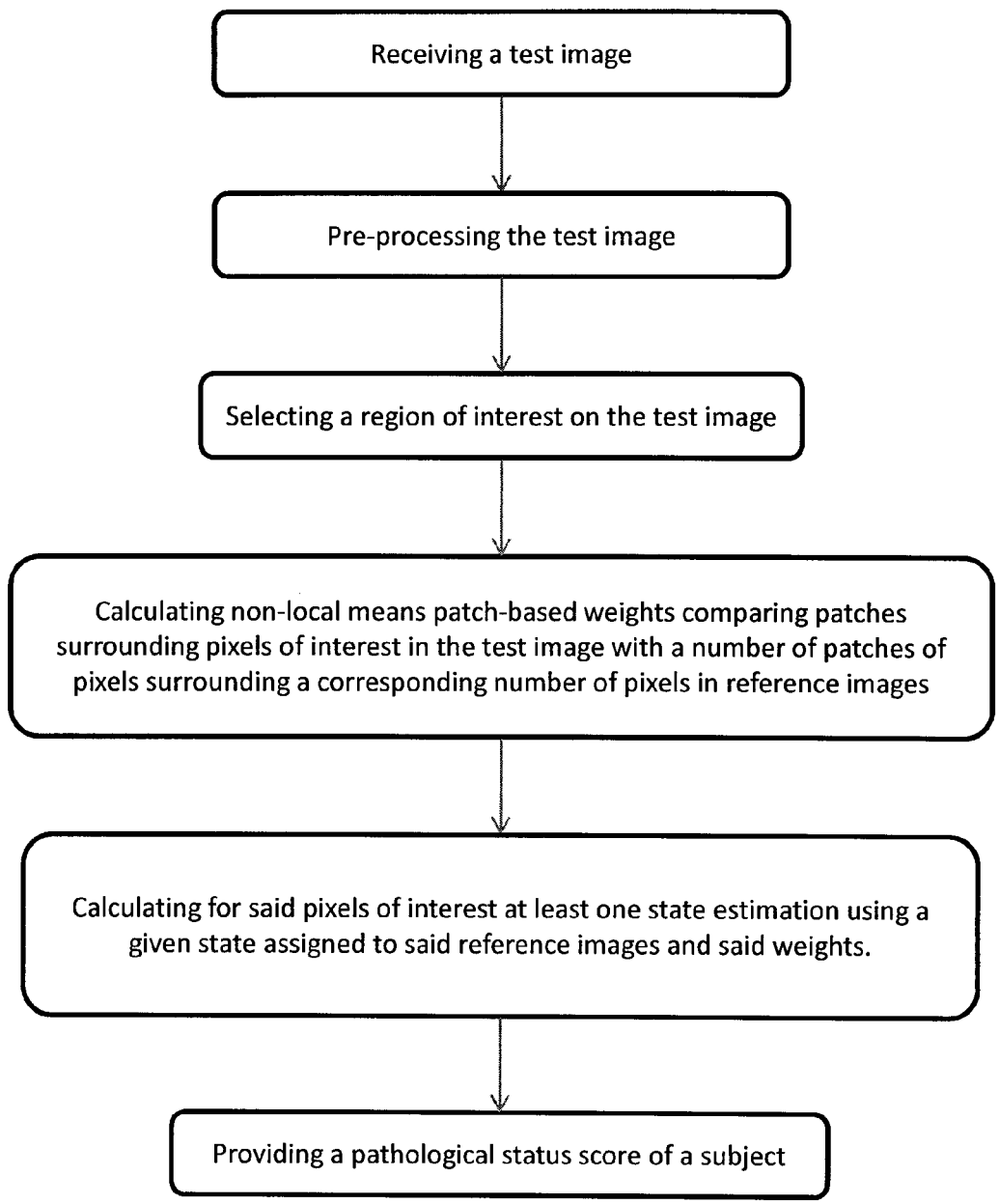
FIG. 8 shows a method of segmenting and grading structures according to the present invention.

FIG. 8 shows one preferred method of segmenting and grading according to the present invention. The method comprises receiving a test image; pre-processing the test image; selecting a region of interest on the test image; calculating non-local means patch-based weights comparing patches surrounding pixels of interest in the test image with a number of patches of pixels surrounding a corresponding number of pixels in reference images; calculating for the pixels of interest at least one state estimation using a given state assigned to the reference images and the weights; and providing a pathological state score of a subject.

Figure 11:
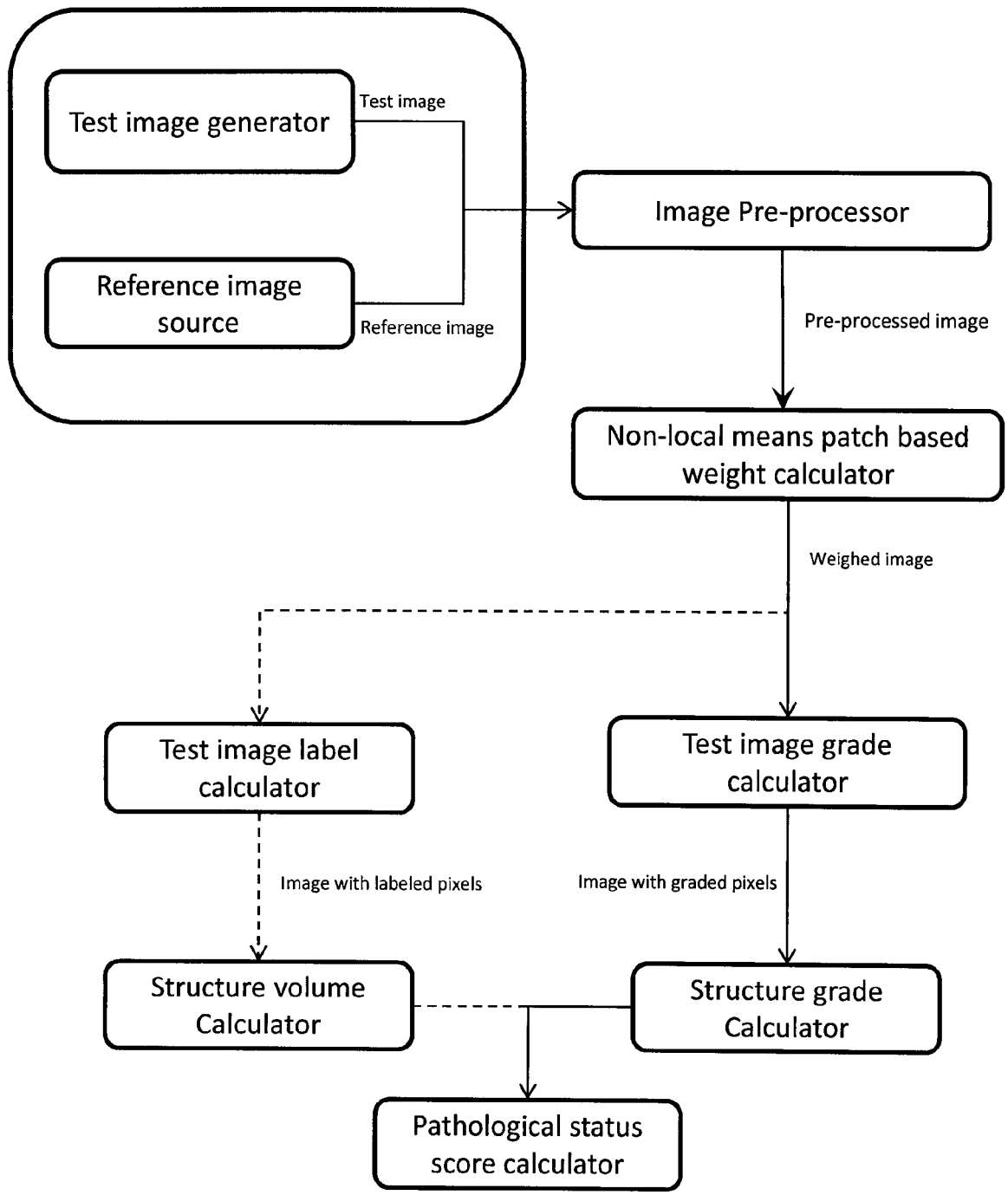
FIG. 11 shows a block diagram illustrating various components of an apparatus (processor) for segmentation and grading of medical images.

It will be appreciated that all aspects of the above method can be performed by a computer using software programmed to carry out the described method (see FIG. 11).

Figure 9:
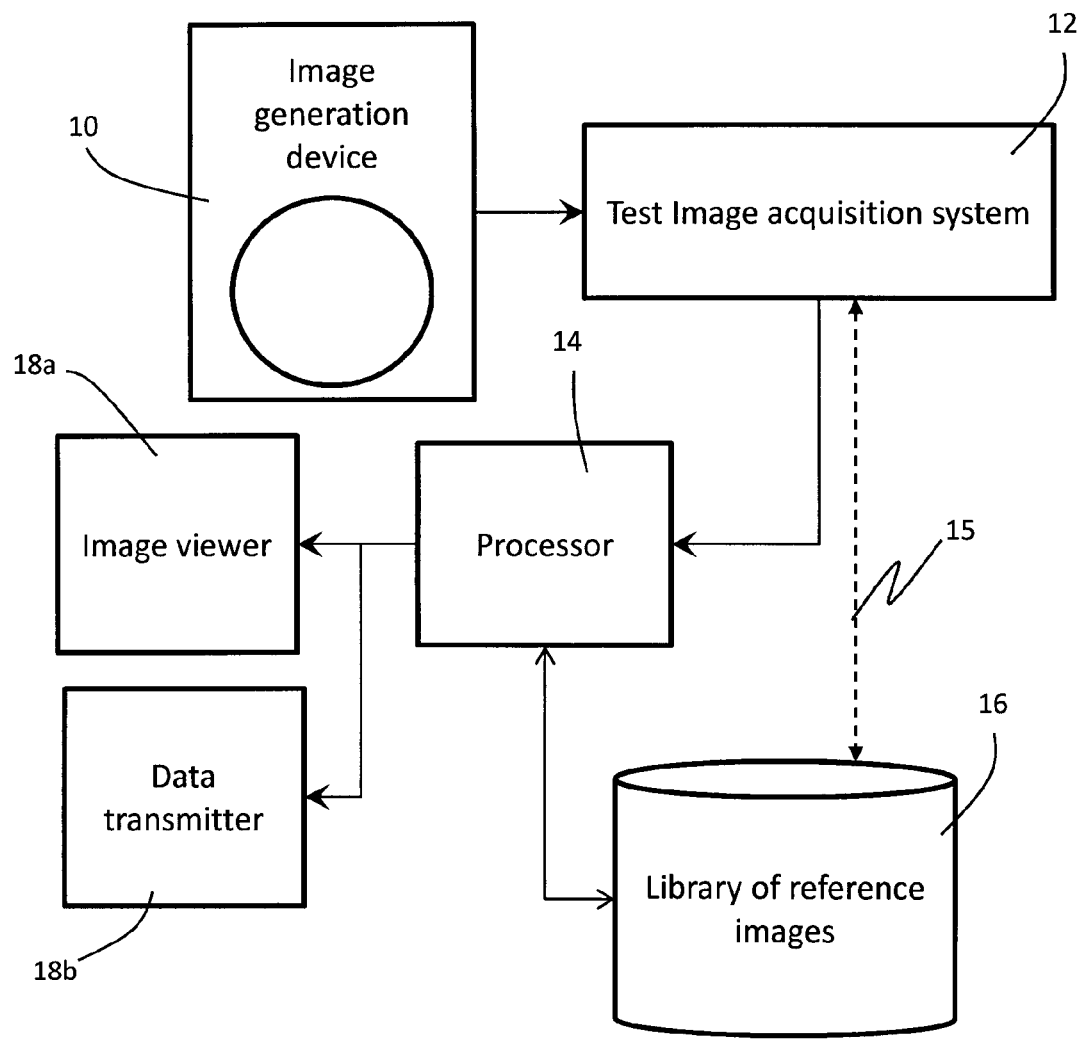
FIG. 9 shows a block diagram illustrating various components of an apparatus for segmentation and grading of structures.

FIG. 9 is a block diagram illustrating one possible physical setup of the present invention. In this setup, a subject is placed inside an image generation device 10 (in this case, an MRI machine) to generate an image of his brain. The imaging is performed by radio frequency emitters/sensors that are placed inside the MRI machine. The RF sensors send data to an image acquisition system 12 for acquiring data that will be used to generate images of the brain. A library of reference images 16 is compared to the test image in the processing step to determine grading and/or volume of a structure for state determination. The image can be pre-processed and processed in a processor 14. After the various processing steps occurring in the processor 14 (shown in more detail in FIG. 11), the image-data-state-score is ready to be viewed on an viewer 18a or transmitted via a data transmitter 18b. In some cases, the test image belongs to a subject for which a medical diagnosis has been reliably obtained. In such cases, the test image can be directly incorporated into the Library of reference images or the processor can seed the library with the images for which the diagnosis is known. The method and apparatus of the present invention rely critically on the reference images in the library and the more images are used in the calculations, the more reliable is the pathological state score, state and volume estimation. It is therefore advantageous to increase the number of reference images for which a medical diagnosis is known. One way to achieve this would be to anonymize the test images with a code such that when a patient receives a medical diagnosis, the reference library is automatically updated with the information.

Figure 10:
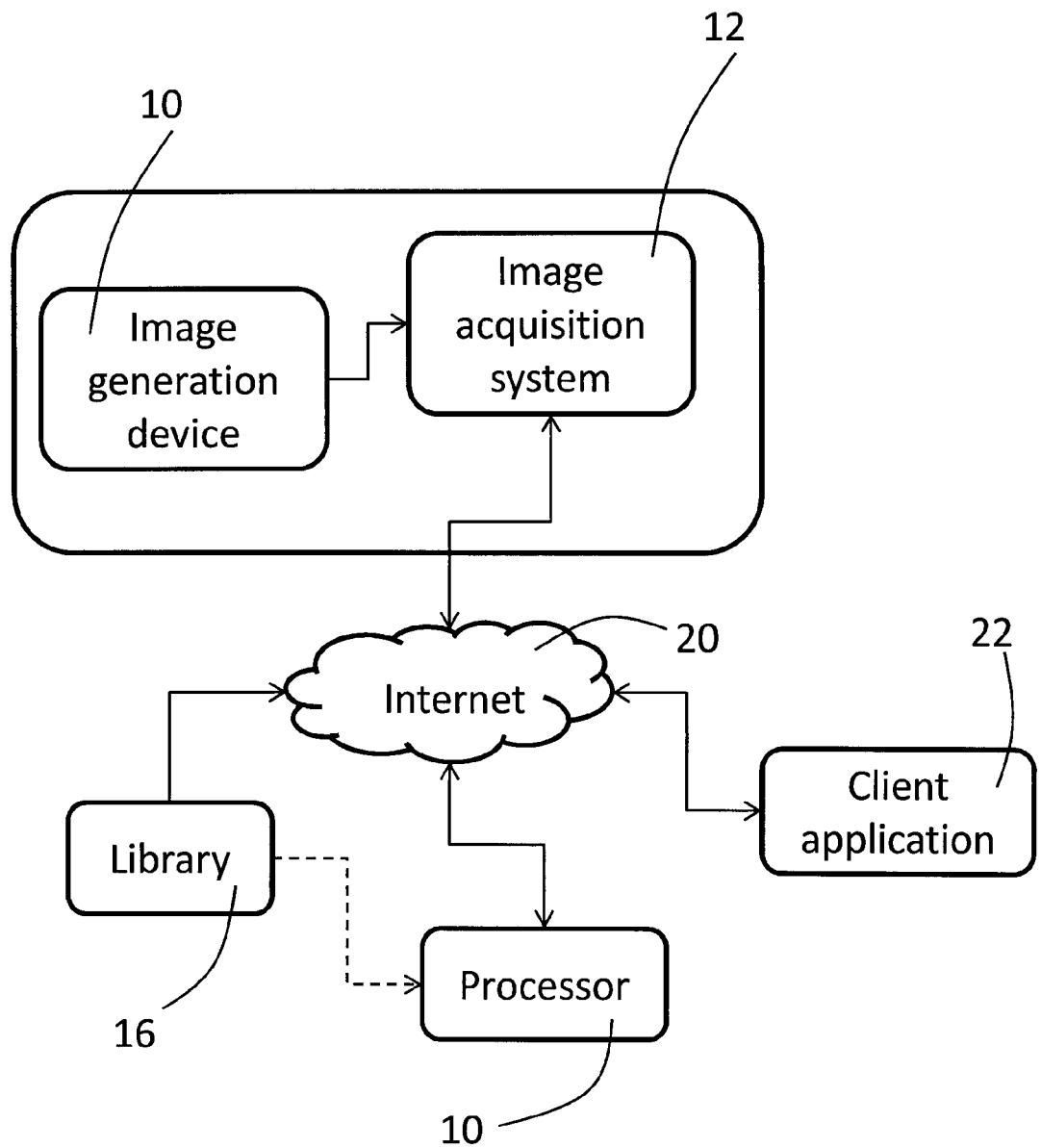
FIG. 10 shows a block diagram illustrating a physical embodiment of an apparatus for segmentation and grading of medical images.

FIG. 10 shows an alternate embodiment of the present invention where the image generation device 10 and the image acquisition system 12 are not in the same physical location as the processor 14, and wherein an image acquisition system 12 sends via the data transmitter 18b the image data through a network 20 (such as the internet). The data output from the transmitter can be returned to the image acquisition system 12 or to an alternate location 22, such as a doctor's computer/office or the subject's computer/home.

FIG. 11 shows a block diagram illustrating a physical embodiment of a processor 14 for calculating segmentation and grading of medical images. In this processor, a test image and a plurality of reference images are received and pre-processed, non-local means patch-based weight calculator generates weighted image data that is used by the test image grade calculator and possibly the test image label calculator. All pixels of the patch located in the region of interest of an MRI image graded and possibly labelled (structure or non-structure) for segmentation. The grade data is used (possibly in conjunction with the volume data) to calculate a pathological state score, thus informing a subject about whether his "structure" correlate's more with those of healthy or diseased reference image structures.

Table 3 shows the success rates obtained by the proposed imaging biomarkers (i.e., HC volume, HC score, HC–EC volume, HC–EC score) for AD vs. CN, MCIp vs. CN, and MCIp vs. MCIs.

First, the SNIPE results show that grading-based biomarkers outperform volume-based biomarkers. Moreover, the HC-grade and HC–EC complex grade provided similar results. As expected, classification accuracies decrease when populations with more similar pathological state are used. Thus, the lowest accuracy was obtained for the MCIp vs. Mas experiment.

For AD vs. CN, SNIPE obtained similar results to the combination of 4 methods as proposed in Wolz et al. (90% here compared to 89%). However, SNIPE obtained better results than HC volume, manifold-based learning, CTH and TBM; although TBM obtained results close to those of SNIPE. However, it should be noted that SNIPE does not require nonlinear registration contrary to TBM and thus is less computationally expensive (i.e., around 5 minutes of processing).

For MCIp vs. CN, SNIPE obtained better results than all the methods compared in Wolz et al. (2010) as well as their combination (88% compared to 84%). Moreover, these results are close to the results obtained by SNIPE for AD vs. CN. This seems to indicate that the MCIp subjects can be as reliably classified as the AD population indicating that the SNIPE technique with the inclusion of HC and EC grade is better able to distinguish MCIp from CN than other multi-methods used in other reports.

For MCIp vs. MCIs, SNIPE obtained clearly better results than all the methods compared in Wolz et al. (74% compared to 68%). These worst results compared to MCIp vs CN, could be explained by the heterogeneity of Mas group including a mix of individuals including some who will convert to AD as well as others who will not. In any case, these results highlight the potential of SNIPE for AD prediction by enabling the detection of anatomical changes caused by AD at the early stages of the pathology.

Finally, it is noted that HC volume-based classification obtained with patch-based label fusion yielded results similar to those based on multi-atlas label fusion.

TABLE 3

Imaging Biomarker Comparison. Results obtained for AD vs. CN, MCIp vs. CN and MCIp vs. MCIS using 100 x LNOCV for several imaging biomarkers

|  | AD vs. CN | MCIp vs. CN | MCIp vs. MCIs |
| --- | --- | --- | --- |
| SNIPE |  |  |  |
| HC Volume | 82 | 78 | 66 |
| HC Grade | 90 | 87 | 74 |
| HC-EC Volume | 81 | 77 | 67 |
| HC-EC Grade | 90 | 88 | 73 |
| Multi-Method (Wolz et al.) |  |  |  |
| HC Volume | 81 | 76 | 65 |
| Manifold learning | 85 | 78 | 65 |
| Cortical thickness | 81 | 77 | 56 |
| TBM | 87 | 79 | 64 |
| All | 89 | 84 | 68 |

It has been observed that, some cases, EC atrophy appears earlier than HC atrophy and thus could be a better temporal predictor (biomarker) of MCI and/or AD. It will be appreciated that non-local mean refers to the method of Buades for denoising images presented in (reference Buades 2005).

It will be appreciated that other structures can be used to improve state estimation results and the method of the present invention can be applied to other diseases. It is understood that the term structure is not limited to the brain and can be any structure identified in an image. Without limiting structures that can be identified in an image, the structure can be, for example, a hippocampus, an entorhinal cortex, a nuclei, an organ, a muscle, a breast, a blood vessel, a gland a cartilage, a ligament and a bone.

It will be appreciated that, throughout this description the term state includes the state of a disease (including health), as well as a state of being, or not, a structure of interest. For example, for segmentation purposes, state (also referred to as label in some cases) can refer to being the structure or not being the structure, and can be an all or none value whereas for a pathological state estimator, the state can be a degree of likelihood of being diseased, or a similarity to images of diseased brains.

In other embodiments, the structure can actually be void of any tissue and thus defined by its inner or outer surface. The structure can also be a space filled with a fluid (cerebrospinal fluid) such the ventricles.

It will be appreciated that the term subject refers to any person whose image has been subjected to the method or apparatus of the present invention. The subject can be healthy or diseased. The "pathological state" is a continuum from completely healthy to completely diseased. Healthy subjects can perform longitudinal studies according to the present invention to estimate their health and this should be understood as calculating a pathological state that can result in a state of: completely healthy. It will be appreciated that, in some embodiments, the pathological state can be prognostic rather than diagnostic.

It will be appreciated that the method and apparatus of the present invention can be used in longitudinal or multi-modal studies in order to determine, for example, tumor size/growth rate/progression.

Although the present document presents one way of selecting and weighing patches, many other methods could be used to achieve this goal. For example, patch selection and weighting can be based on subject's age, gender or other clinical data such as MMSE score, genetic phenotype, or other clinical data.

Reference images can be obtained, among others, from a template library, from a collection of pre-labelled datasets, from a collection of datasets from subjects with known pathological states.

In some embodiments of the present invention, the test image subject's age can be matched to the reference images subjects' age (library) in order to increase efficiency of the state.

Averaging a grade (g) within a structure may be sub-optimal and more optimal weighing (e.g. multi-variate logistic regression) could be found to weigh both within anatomical structures (i.e., anterior part of HC is more diagnostic) or between structures. For example, it has been observed that the Ca1, Ca4 and subicular regions of the hippocampus offer a better clinical state estimate. Weightings could be optimized over scales and regressions of grade versus time-to-conversion (or time-to-event) could be used to estimate time to convert from MCI to AD.

The terms Pixel and Voxel are used interchangeably in this document and the invention works in 2 dimensions (2D), 3 dimensions (3D) and n dimensions using either a single modality or multiple modalities. The image can be multi-dimensional, for example a 2D set of pixels, a 3D set of voxels, a 3D dataset comprising of 2D pixels acquired over time, a 4D dataset of 3D voxels over time, a 4D dataset of 3D voxels where each voxel is represented by a spectrogram.

The term network should be understood as including internal networks, the internet and any displacement of any type of physical media such as CDs and flash memory from one place to another.

The term image in the present invention refers to any image such as an image generated in a magnetic resonance imaging (MRI), positron-emission tomography (PET), computerized tomography (CT), fluoroscopy, X-ray, etc.

Among the advantages of the present invention for medical professionals are increasing productivity, increasing confidence in diagnosis, increasing confidence in treatment plans, leveraging state-of-the-art knowledge, enabling personalized medicine, allowing to predict if a patient will benefit from a particular drug. Among the advantages of the present invention for pharmaceutical companies are allowing to determine if a patient will benefit from a particular drug, using the present invention as a selection and an enrichment tool for clinical trials by decreasing sample size and/or targeting responders.

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

What is claimed is:

1. A computer-implemented method for performing segmentation on medical images, the method comprising:
    positioning a subject in an image generation device and acquiring a test image dataset of the subject;
    providing to a processor the test image dataset and a library of reference image datasets, said reference image datasets defining for each pixel or voxel a structure segmentation value;
    performing registration of said test image dataset and said library of reference image datasets;
    selecting a region of interest of said test image dataset, patch dimensions and a search window dimensions;
    for each pixel or voxel of said region of interest of said test image dataset:
        defining a test patch of said patch dimensions centered on said pixel or voxel;
        for each reference image dataset of said library of reference image datasets:
            define a search window of said window dimensions in said reference image centered on said pixel or voxel
            for each window pixel or voxel in said search window:
                calculating, across all pixels or voxels within said patch dimensions centered on said pixel in said search window, a similarity value with all pixels or voxels of said test patch in said test image;
                recording said similarity value and the corresponding structure segmentation value;
            determining the most appropriate structure segmentation value for said pixel or voxel of said region of interest of said test image dataset from said recorded similarity values and said corresponding structure segmentation values;

modifying a computer-displayable image dataset of said test image dataset using said structure segmentation value for said each pixel or voxel of said region of interest of said test image dataset.

2. The method of claim 1, wherein said structure segmentation value is binary and represents structure or non-structure, said determining comprises using a formula:

$$v(x_i) = \frac{\sum_{s=1}^{N} \sum_{j \in \Omega} w(x_i, x_{s,j}) \cdot l(x_{s,j})}{\sum_{s=1}^{N} \sum_{j \in \Omega} w(x_i, x_{s,j})}$$

where l is said structure segmentation value (0 for non-structure and 1 for structure), w( ) is said similarity value, $x_i$ is the pixel or voxel of interest of the test image, $x_{s,j}$ is a pixel or voxel in reference image s, $\Omega$ is the set of pixels or voxels in the said region of interest, and a pixel or voxel $v(x_i)$ is segmented as structure when $v(x_i)$ is greater than 0.5.

3. The method of claim 2, wherein said medical images are brain images.

4. The method of claim 1, further comprising calculating and storing mean and standard deviation values for said patch dimensions for pixels or voxels in said library of reference image datasets and said test image dataset, wherein said calculating a similarity value comprises comparing said mean and standard deviation values to select a patch from a reference image.

* * * * *